(12) United States Patent
Yu et al.

(10) Patent No.: US 8,846,623 B2
(45) Date of Patent: Sep. 30, 2014

(54) CANCER-TARGETING PEPTIDES AND USES THEREOF IN CANCER TREATMENT AND DIAGNOSIS

(75) Inventors: John Yu, Taipei (TW); Alice L. Yu, Taipei (TW); H. C. Wu, Taipei (TW); Sheng-Hung Wang, Taichung (TW); I-Ju Chen, Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 13/816,613

(22) PCT Filed: Oct. 25, 2011

(86) PCT No.: PCT/US2011/057637
§ 371 (c)(1),
(2), (4) Date: Feb. 12, 2013

(87) PCT Pub. No.: WO2012/061113
PCT Pub. Date: May 10, 2012

(65) Prior Publication Data
US 2013/0142867 A1    Jun. 6, 2013

Related U.S. Application Data

(60) Provisional application No. 61/455,781, filed on Oct. 25, 2010.

(51) Int. Cl.
| | | |
|---|---|---|
| A61K 38/00 | (2006.01) | |
| A61K 31/496 | (2006.01) | |
| A61K 47/48 | (2006.01) | |
| A61K 45/06 | (2006.01) | |
| A61K 38/10 | (2006.01) | |
| A61K 49/00 | (2006.01) | |
| C07K 5/117 | (2006.01) | |
| A61K 31/337 | (2006.01) | |
| C07K 7/08 | (2006.01) | |
| A61K 31/475 | (2006.01) | |
| A61K 51/12 | (2006.01) | |
| A61K 31/704 | (2006.01) | |
| A61K 9/127 | (2006.01) | |

(52) U.S. Cl.
CPC .......... *C07K 7/08* (2013.01); *A61K 9/1271* (2013.01); *G01N 2333/47* (2013.01); *A61K 31/496* (2013.01); *A61K 47/48815* (2013.01); *A61K 45/06* (2013.01); *A61K 38/10* (2013.01); *A61K 49/0043* (2013.01); *C07K 5/1024* (2013.01); *G01N 2500/04* (2013.01); *A61K 31/337* (2013.01); *A61K 9/127* (2013.01); *A61K 31/475* (2013.01); *A61K 49/0056* (2013.01); *A61K 51/1234* (2013.01); *A61K 31/704* (2013.01)
USPC .......... 514/19.3; 530/324; 530/325; 530/326; 530/327; 530/328

(58) Field of Classification Search
None
See application file for complete search history.

(56) References Cited

U.S. PATENT DOCUMENTS

| | | | | |
|---|---|---|---|---|
| 5,705,610 | A  * | 1/1998 | Zuckermann et al. | 530/338 |
| 6,500,920 | B1 * | 12/2002 | Haung | 530/328 |
| 7,030,295 | B2 * | 4/2006 | Chen et al. | 800/302 |
| 7,173,058 | B2 * | 2/2007 | Muller et al. | 514/417 |
| 7,238,665 | B2 | 7/2007 | Wu et al. | |
| 7,557,088 | B2 * | 7/2009 | Skubatch | 514/1.1 |
| 8,039,440 | B2 | 10/2011 | Peled et al. | |
| 8,268,964 | B2 * | 9/2012 | Scholler et al. | 530/350 |
| 8,362,207 | B2 * | 1/2013 | Debinski et al. | 530/351 |
| 8,394,758 | B2 | 3/2013 | Wu et al. | |
| 2003/0166004 | A1 | 9/2003 | Gyuris et al. | |
| 2004/0002052 | A1 | 1/2004 | Hendry | |
| 2004/0171552 | A1 | 9/2004 | Peled et al. | |
| 2007/0156342 | A1 | 7/2007 | Frimurer et al. | |
| 2007/0197446 | A1 | 8/2007 | Schwabe et al. | |
| 2008/0003200 | A1 | 1/2008 | Arap et al. | |
| 2008/0193510 | A1 | 8/2008 | Wu et al. | |
| 2010/0119511 | A1 | 5/2010 | Wang et al. | |
| 2010/0137225 | A1 | 6/2010 | Herman et al. | |
| 2010/0173848 | A1 | 7/2010 | Peled et al. | |
| 2010/0221183 | A1 | 9/2010 | Squires | |
| 2012/0028913 | A1 | 2/2012 | Peled et al. | |

FOREIGN PATENT DOCUMENTS

| | | | |
|---|---|---|---|
| WO | WO 03/037172 | A2 | 5/2003 |
| WO | WO 03/072599 | A2 | 9/2003 |
| WO | WO 2004/071457 | A2 | 8/2004 |
| WO | WO 2008/073162 | A2 | 6/2008 |
| WO | 2008/085828 | * | 7/2008 |

OTHER PUBLICATIONS

Brand et al., Anticancer Res. 2006; 26:463-70.*

Arap et al., Cell surface expression of the stress response chaperone GRP78 enables tumor targeting by circulating ligands. Cancer Cell. Sep. 1, 2004;6(3):275-84.

Chang et al., Antiangiogenic targeting liposomes increase therapeutic efficacy for solid tumors. J Biol Chem. May 8, 2009;284(19):12905-16. doi: 10.1074/jbc.M900280200. Epub Mar. 10, 2009.

(Continued)

*Primary Examiner* — Sheela J Huff
(74) *Attorney, Agent, or Firm* — Wolf, Greenfield & Sacks, P.C.

(57) ABSTRACT

Cancer-targeting peptides having a $PX_1LX_2$ motif, in which $X_1$ is His or an amino acid residue with a hydrophobic side chain and $X_2$ is Pro, Phe, or Trp. Also disclosed herein are conjugates containing the cancer-targeting peptides and uses thereof in cancer treatment and diagnosis.

20 Claims, 12 Drawing Sheets

(56) References Cited

OTHER PUBLICATIONS

Dickerson, The protein and peptide mediated syntheses of non-biologically-produced oxide materials, Paper for doctoral degree, (2007), School Materials Science and Engineering, Georgia Institute of Technology.

Kuo et al., Identification of Oral Cancer-Targeted Peptides by in vivo Phage Display and Ligand-targeted Therapy for Anti-angiogenic Therapy, Student Thesis of National Taiwan University, 2004.

Willerth et al., Rationally designed peptides for controlled release of nerve growth factor from fibrin matrices, J. Biomedical Materials Research (2006, online publication), 80(1): p. 13-23.

Extended European Search Report mailed Apr. 11, 2014 for European Application No. EP 11838514.5.

Holmes et al., Cloning and characterization of ZNF236, a glucose-regulated Kruppel-like zinc-finger gene mapping to human chromosome 18q22-q23. Genomics. Aug. 15, 1999;60(1):105-9.

No Author Listed, Hydrophobicity scales, Wikipedia, the free encyclopedia, htip://en.wikipedia.org, last accessed on Mar. 27, 2014, 9 pages.

* cited by examiner

Generation of optimized cancer targeting peptides

CANCER-TARGETING PEPTIDES AND USES THEREOF IN CANCER TREATMENT AND DIAGNOSIS

RELATED APPLICATION

This application is a national stage filing under 35 U.S.C. 371 of International Application PCT/US2011/057637, filed Oct. 25, 2011, which claims priority to U.S. Provisional Application No. 61/455,781, filed on Oct. 25, 2010, the content of which is hereby incorporated by reference herein.

A Sequence Listing is provided herein as an ASCII text file, which was created on Feb. 12, 2013 and has a file name of "A0988.70018US01-SEQ.txt" and a file size of 7 KB. The material in this ASCII text file is herein incorporated by reference in its entirety.

BACKGROUND OF THE INVENTION

The use of peptides as targeted delivery agents is a rapidly emerging field applicable to treatment of a variety of diseases, such as cancer, metabolic diseases, inflammatory autoimmune diseases, and viral infection. Wang et al. *Expert Opin. Drug Deliv.* 7:159-171 (2010); Liu, *Bioconjug. Chem.* 20: 2199-2213 (2009); Hsu et al. *BioDrugs.* 23:289-304 (2009); Bellmann-Sickert et al. *Trends Pharmacol. Sci.* 31:434-441 (2010); Zhong, *Curr. Top Med. Chem.* 10:386-396 (2010); and Briand et al. *Curr. Pharm. Des.* 16:1136-1142 (2010). A number of cancer-targeting peptides have been identified, which specifically bind to various cancer markers, including integrin, vascular endothelial growth factor (VEGF), and heat-shock protein 90 (Hsp90). Wang et al., 2010; Hsu, 2009; and Horibe et al. *J. Transl. Med.* 9:8 (2011) Most of these cancer-targeting peptides have been used in the treatment of neuroendocrine tumors.

It is of great interest to develop new cancer-targeting peptides for use in diagnosing and treating a broad spectrum of cancers.

SUMMARY OF THE INVENTION

The present disclosure is based on the identification of a number of peptides that target human glucose-regulated protein 78 (GRP78), a protein expressed on the surface of various types of cancer cells, via computational design.

Accordingly, one aspect of the present disclosure relates to an isolated peptide comprising an amino acid sequence motif $PX_1LX_2$ (SEQ ID NO:1) in which $X_1$ is H or an amino acid with a hydrophobic side chain (e.g., L, F, or W) and $X_2$ is P, F, or W. Preferably, when $X_1$ is L, $X_2$ is not P; and when $X_2$ is P, $X_1$ is not L. In some embodiments, the isolated peptide comprises the amino acid sequence of $RLLDTNRPX_1LX_2Y$ (SEQ ID NO:2). Examples include, but are not limited to, RLLDTNRPFLPY (P-6) (SEQ ID NO:3), RLLDTNR-PHLWY (P-12) (SEQ ID NO:4), and RLLDTNRPFLFY (P-13) (SEQ ID NO:5).

In another aspect, the present disclosure provides a composition comprising (a) any of the cancer-targeting peptide disclosed herein, and (b) an anti-cancer agent (e.g., doxorubicin, vinorelbine, vincristine, paclitaxel or lurtotecan), a detectable label (e.g., a fluorescent compound such as fluorescein isothiocyanate or a luminescent compound), or both. In some embodiments, the cancer-targeting peptide and the anti-cancer agent or the detectable label are conjugated (attached), either directly or via a linker (e.g., a polymer such as polyethylene glycol). The composition can further comprise a vehicle carrier such as a liposome. In some embodiments, the vehicle carrier encapsulates the anti-cancer agent, the detectable label, or both. The detectable label can be an imaging agent suitable for tumor imaging (e.g., a radioactive molecule such as $^{99m}$Tc or $^{188}$Re. or an iron oxide nanoparticle). The cancer-targeting peptide, preferably pegylated, can be attached on the surface of the vehicle carrier.

The composition described above can be a pharmaceutical composition, which can further comprise a pharmaceutically acceptable carrier. In some embodiments, the composition contains an anti-cancer agent in an amount effective in treating cancer. In other embodiments, the composition contains a detectable label such as an imaging agent in an amount effective in detecting cancerous tissues and/or cells.

In addition, the present disclosure also provides a method for delivering an anti-cancer agent or a detectable label to cancer cells, e.g., breast cancer cells (such as breast cancer stem cells), hepatocellular carcinoma cells, prostate cancer cells, lung cancer cells, ovarian cancer cells, kidney cancer cells, uterine cervical cancer cells, melanoma cells, embryonal carcinoma cells, leukemia cells, or osteosarcoma cells. The method comprises contacting cancer cells or cells suspected to be cancerous with any of the compositions described herein. The composition can be administered to a subject in need thereof (e.g., a human patient having or suspected of having cancer). Alternatively, it can be incubated (in vitro) with a sample (e.g., a tissue sample) having or suspected of having cancer cells. In some embodiments, the anti-cancer agent is delivered to a subject in an amount effective in treating cancer. In other embodiments, a detectable label, preferably an agent suitable for cancer imaging, is delivered to a subject in need thereof (e.g., a human patient having or suspected of having a solid tumor) in an amount effective in detecting cancer cells and/or cancerous tissues.

Also within the scope of this disclosure are any of the pharmaceutical compositions described herein for use in delivering one or more anti-cancer agents, one or more detectable labels, or both to cancer cells, for use in cancer treatment and/or diagnosis, as well as using these compositions in manufacturing a medicament for the above-noted purposes.

Further, the present disclosure provides a method for identification (structure-based optimization) of a cancer-targeting peptide ligand. The method comprises: (a) providing a cancer cell-surface protein (e.g., human GRP78); (b) calculating the Connolly surface of the cancer cell-surface protein by, e.g., a binding pocket analysis program such as PscanMS; (c) identifying a peptide-binding site on the protein surface; (d) estimating distance-dependent potential of paired atoms involved in polar interactions (e.g., hydrogen bonding, ionic interactions and metal-ion coordination), the estimation comprising consideration of an intermolecular surface distance; (e) estimating distance-dependent potential of paired atoms involved in non-polar interactions, the estimation comprising application of Connolly surface of protein in calculation of the intermolecular surface distance; and (f) selecting a peptide ligand optimized for binding to the binding site of the cancer cell-surface protein from a peptide database, which can be combinatorially constructed, based on the information obtained from steps (d) and/or (e). In one example, the intermolecular surface distance is determined based on the binding energy ($\Delta E$) between protein (p) and ligand (l), which is calculated according to the following equation:

$$\Delta E_{p,l} = \Delta E_{polar}(\delta, \theta, \phi) + \Delta E_{non-polar}(v, A) \qquad , (\phi < 100°)$$

$$= F_{hbond} \times \sum_h (\cos(180° - \theta_h) \times W_{hbond}(\delta_h)) +$$

$$F_{ion} \times \sum_i W_{ion}(\delta_i) + F_{metal} \times \sum_m W_{metal}(\delta_m) +$$

$$F_{vdw} \times \sum_v (A_v \times W_{vdw}(v_v))$$

wherein, h is the pair of H-bond; i is the pair of ionic interaction; m is the pair of metal-ion coordination and v is the ligand-contacted normal vector in hydrophobic interaction.

The distance-dependent potentials can be predicted from a statistical set comprising occurrence frequencies of paired pharmacophores in molecular interactions.

In other embodiments, the just-described method is performed in silico (i.e., performed on computer or via computer simulation).

The details of one or more embodiments of the invention are set forth in the description below. Other features or advantages of the present invention will be apparent from the following drawings and detailed description of several embodiments, and also from the appended claims.

BRIEF DESCRIPTION OF THE DRAWINGS

The drawings are first described.

DETAILED DESCRIPTION OF THE INVENTION

Figure 1:
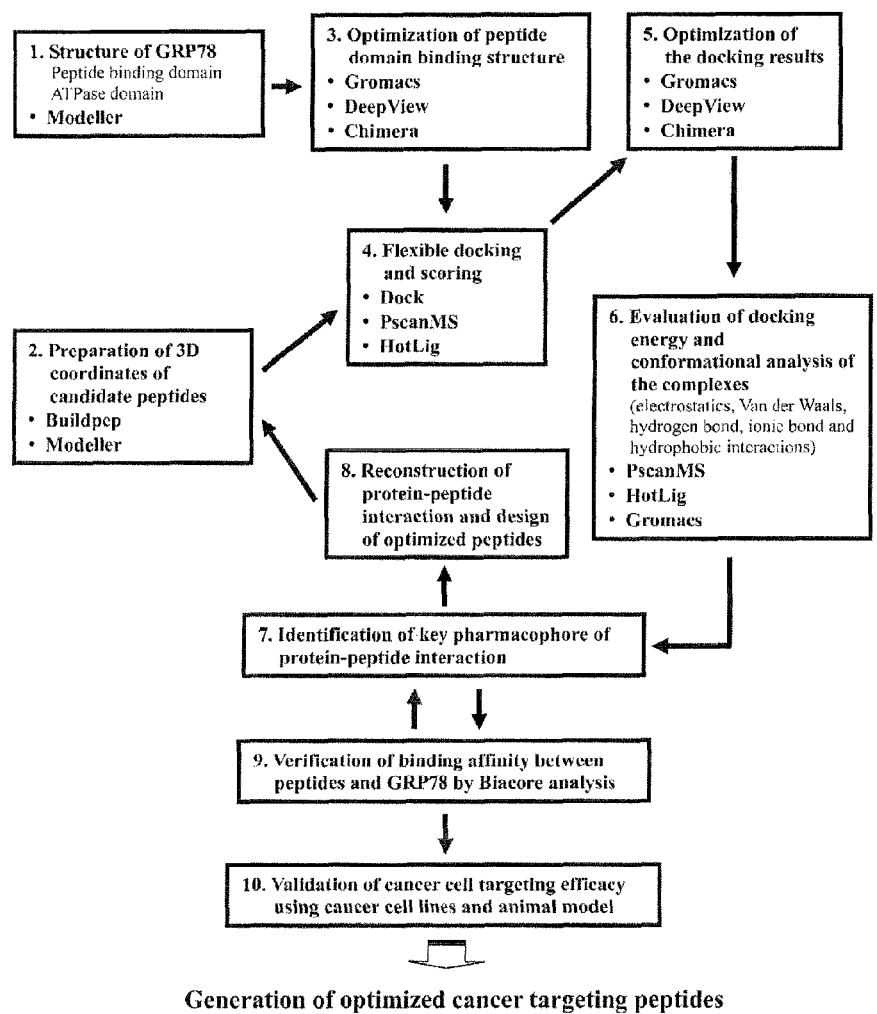
FIG. 1 is a schematic illustration of the design of optimized peptides targeting human cancer marker proteins (using human GRP as an example) in silico.

Disclosed herein are cancer-targeting peptides, which are capable of binding to human GRP78, compositions comprising (a) one or more of the cancer-targeting peptides, and (b) one or more anti-cancer agents, one or more detectable labels, or both. These peptides are capable of targeting GRP78, which was found to be expressed on a broad spectrum of cancer cells. Accordingly, the cancer-targeting peptides described herein can be used for delivering anti-cancer agents and/or detectable labels to various cancers, particularly those that express GRP78 on cell surfaces, thereby facilitating cancer diagnosis and treatment.

(i) Cancer-Targeting Peptides and Conjugates Containing Such

The isolated cancer-targeting peptides disclosed herein each comprise an amino acid sequence motif Pro-$X_1$-Leu-$X_2$ (also known as P$X_1$L$X_2$) (SEQ ID NO:1), in which $X_1$ is His or an amino acid residue having a hydrophobic side chain and $X_2$ is Pro, Phe, or Trp. $X_1$ can be an amino acid residue having a aliphatic hydrophobic side chain, e.g., Ala, Ile, Leu, or Val. Alternatively, $X_1$ can be an amino acid residue having an aromatic hydrophobic side chain, e.g., Phe, Trp, or Tyr. In addition, $X_1$ can also be Gly, Met, or Pro. Examples of the motifs include, but are not limited to, PFLP (SEQ ID NO:6), PHLW (SEQ ID NO:7), PFLW (SEQ ID NO:8), PYLW (SEQ ID NO:9), and PFLF (SEQ ID NO:10). Preferably, when $X_1$ is Leu, $X_2$ is not Pro, and when $X_2$ is Pro, $X_1$ is not Leu. When desired, the cancer-targeting peptides can include the any of the above disclosed $PX_1LX_2$ (SEQ ID NO:1) motif and a R residue and a Y residue at the N-terminal and C-terminal of the motif, respectively.

In some embodiments, the cancer-targeting peptides described herein comprises the amino acid sequence of RLLDTNRPX$_1$LX$_2$Y (SEQ ID NO:2), in which the motif PX$_1$LX$_2$ is described above. Examples of the cancer-targeting peptides include, but are not limited to, RLLDTNRPFLPY (P-6; SEQ ID NO:3), RLLDTNRPHLWY (P-12; SEQ ID NO:4), RLLDTNRPFLFY (P-13; SEQ ID NO:5), RLLDTNRPFLWY (PB-1; SEQ ID NO:11); and RLLDTNRPFLFY (PB-2; SEQ ID NO:12). In other embodiments, the cancer-targeting peptides described herein each consist of the PX$_1$LX$_2$ motif described herein, or consists of the motif and a R residue and a Y residue at the N-terminal and C-terminal of the motif, respectively.

The term "peptide" used herein refers to a polymer composed of two or more amino acid monomers and is shorter than a protein. Preferably, each of the cancer-targeting peptides described herein includes up to 50 (e.g., up to 20 or 30) amino acids. In some examples, the cancer-targeting peptides each contain 4-20 amino acid residues (e.g., 4-10, 6-10, 6-15, or 6-20 amino acid residues). These peptides can contain naturally-occurring amino acid residues, or modified amino acids. In one example, either the N-terminus or the C-terminus of a cancer-targeting peptide is modified, e.g., containing an —NH$_2$ group at the C-terminus. An "isolated" peptide is a peptide that is substantially free from naturally associated molecules, i.e., the naturally associated molecules constituting at most 20% by dry weight of a preparation containing the polypeptide. Purity can be measured by any appropriate method, e.g., column chromatography, polyacrylamide gel electrophoresis, and HPLC.

The cancer-targeting peptides described herein can be made by any conventional methods, e.g., recombinant technology or standard methods of solid phase peptide chemistry well known to any one of ordinary skill in the art. For example, the peptides may be synthesized by solid phase chemistry techniques following the procedures described by Steward et al. in Solid Phase Peptide Synthesis, 2nd Ed., Pierce Chemical Company, Rockford, Ill., (1984) using a Rainin PTI Symphony synthesizer. For solid phase peptide synthesis, techniques may be found in Stewart et al. in "Solid Phase Peptide Synthesis", W. H. Freeman Co. (San Francisco), 1963 and Meienhofer, Hormonal Proteins and Peptides, 1973, 246. For classical solution synthesis, see for example Schroder et al. in "The Peptides", volume 1, Academic Press (New York). In general, such methods comprise the sequential addition of one or more amino acids or suitably protected amino acids to a growing peptide chain on a polymer. Normally, either the amino or carboxyl group of the first amino acid is protected by a suitable protecting group. The protected and/or derivatized amino acid is then either attached to an inert solid support or utilized in solution by adding the next amino acid in the sequence having the complimentary (amino or carboxyl) group suitably protected and under conditions suitable for forming the amide linkage. The protecting group is then removed from this newly added amino acid residue and the next amino acid (suitably protected) is added, and so forth.

The cancer-targeting peptides described herein can also be prepared by conventional recombinant technology, using expression vectors comprising nucleic acids encoding the cancer-targeting peptides. Such nucleic acids and vectors (e.g., expression vectors) are also within the scope of this disclosure.

The cancer-targeting peptides described herein are capable of binding to human GRP78, which was reported to reside on the outer surface of cancer cells but only in the cytoplasm of normal cells (Lee et al., Cancer Res., 67:3496-3499, 2007; Jakobsen et al., Cancer Res. 67:9507-9517, 2007; Graner et al., Cancer Sci. 100:1870-1879, 2009; and Ni et al., Biochem. J. 434:181-188, 2011). Thus, these peptides can be used to target various types of cancers for, e.g., cancer therapy or diagnosis such as imaging. Target cancers can be, but are not limited to, breast cancer, hepatocellular carcinoma, prostate cancer, lung cancer, ovarian cancer, kidney cancer, uterine cervical cancer, melanoma, embryonal carcinoma, leukemia, osteosarcoma, brain cancer, nasal cancer, pharyngeal cancer, head cancer, neck cancer, bladder cancer, pancreatic cancer, stomach cancer, colon cancer, skin cancer, colorectal, lymphoma, gastric cancer, or leukemia.

Any of the cancer-targeting peptides can be conjugated with (attached to) an anti-cancer agent, a detectable label, or both for cancer treatment and/or cancer diagnosis (either in vivo or in vitro). As used herein, "conjugated" or "attached" means two entities are associated, preferably with sufficient affinity that the therapeutic/diagnostic benefit of the association between the two entities is realized. The association between the two entities can be either direct or via a linker, such as a polymer linker. Conjugated or attached can include covalent or noncovalent bonding as well as other forms of association, such as entrapment, e.g., of one entity on or within the other, or of either or both entities on or within a third entity, such as a micelle.

In one example, a cancer-targeting peptide is attached to a detectable label, which is a compound that allows recognition, either directly or indirectly, the peptide conjugated to it such that the peptide can be detected, measured, and/or qualified. Examples of such "detectable labels" are intended to include, but are not limited to, fluorescent labels, chemiluminescent labels, colorimetric labels, enzymatic markers, radioactive isotopes, and affinity tags such as biotin. Such labels can be conjugated to the peptide, directly or indirectly, by conventional methods.

In some embodiments, the detectable label is an agent suitable for cancer imaging, which can be a radioactive molecule, a radiopharmaceutical, or an iron oxide particle. Radioactive molecules suitable for in vivo imaging include, but are not limited to, $^{122}$I, $^{123}$I, $^{124}$I, $^{125}$I, $^{131}$I, $^{18}$F, $^{75}$Br, $^{76}$Br, $^{77}$Br, $^{211}$At, $^{225}$Ac, $^{177}$Lu, $^{153}$Sm, $^{186}$Re, $^{188}$Re, $^{67}$Cu, $^{213}$Bi $^{212}$Bi, $^{212}$Pb, and $^{67}$Ga. Exemplary radiopharmaceuticals suitable for in vivo imaging include $^{111}$In Oxyquinoline, $^{131}$I Sodium iodide, $^{99m}$Tc Mebrofenin, and $^{99m}$Tc Red Blood Cells, $^{123}$I Sodium iodide, $^{99m}$Tc Exametazime, $^{99m}$Tc Macroaggregate Albumin, $^{99m}$Tc Medronate, $^{99m}$Tc Mertiatide, $^{99m}$Tc Oxidronate, $^{99m}$Tc Pentetate, $^{99m}$Tc Pertechnetate, $^{99m}$Tc Sestamibi, $^{99m}$Tc Sulfur Colloid, $^{99m}$Tc Tetrofosmin, Thallium-201, and Xenon-133. The reporting agent can also be a dye, e.g., a fluorophore, which is useful in detecting tumor mass in tissue samples.

In another example, one of the cancer-targeting peptides described herein is conjugated with an anti-cancer agent to form a treatment conjugate. The anti-cancer agent can be a chemotherapy agent, such as drugs that stop DNA building block synthesis (e.g., methotrexate, fluorouracil, hydroxyurea, lurtotecan, mercaptopurine, pentostatin and pirarubicin), drugs that directly damage DNA (e.g., cisplatin, daunorubicin, doxorubicin, etoposide, teniposide, camptothecin, topotecan, irinotecan, rubitecan, belotecan), drugs that affect mitotic spindle synthesis or breakdown (e.g., vinblastine, vincristine, vinorelbine, vinflunine, vindesine, docetaxel, larotaxel, ortataxel, paclitaxel, tesetaxel, ixabepilone and epithilones), or drugs that disrupt angiogenesis (e.g., anti-VEGF antibody, angiostatin, endostatin, and tumstatin). Alternatively, the anti-cancer agent can be a radiotherapy agent (e.g., $^{90}$Y, $^{125}$I, $^{188}$Re, $^{111}$In DTPA, or $^{131}$I Sodium iodide).

Examples of anti-cancer drugs or antineoplastics to be attached to the cancer-targeting peptides described herein include, but are not limited to, aclarubicin, altretamine, aminopterin, amrubicin, azacitidine, azathioprine, belotecan, busulfan, camptothecin, capecitabine, carboplatin, carmofur, carmustine, chlorambucil, cisplatin, cladribine, clofarabine, cyclophosphamide, cytarabine, daunorubicin, decitabine, doxorubicin, epirubicin, etoposide, floxuridine, fludarabine, 5-fluorouracil, fluorouracil, gemcitabine, idarubicin, ifosfamide, irinotecan, mechlorethamine, melphalan, mercaptopurine, methotrexate, mitoxantrone, nedaplatin, oxaliplatin, paclitaxel, pemetrexed, pentostatin, pirarubicin, pixantrone, procarbazine, pyrimethamine raltitrexed, rubitecan, satraplatin, streptozocin, thioguanine, triplatin tetranitrate, teniposide, topotecan, tegafur, trimethoprim, uramustine, valrubicin, vinblastine, vincristine, vindesine, vinflunine, vinorelbine, and zorubicin.

In any of the conjugates described above, the cancer-targeting peptide can be linked directly to a detectable label or an anti-cancer agent via methods known in the art. Alternatively, the cancer-targeting peptide is linked to a vehicle carrier, which is associated with the detectable label and/or the anti-cancer agent. In one example, the vehicle carrier encapsulates the detectable label and/or the anti-cancer agent. Vehicle carriers include, but are not limited to, micelle, liposome (e.g., cationic liposome), nanoparticle, microsphere, or biodegradable polymer. A cancer-targeting peptide can be tethered to a vehicle carrier by a variety of linkages (e.g., a disulfide linkage, an acid labile linkage, a peptide-based linkage, an oxyamino linkage, or a hydrazine linkage). To improve the association between the peptide and the vehicle carrier, the peptide can be modified by a suitable polymer, such as PEG (peglyated). The detectable label or the anti-cancer agent can be encapsulated within the vehicle via, e.g., association with lipophilic molecules, which can aid in the delivery of the detectable label or the anti-cancer agent to the interior of the vehicle.

In a preferred example, a cancer-targeting peptide described herein is linked to a liposome (as a vehicle carrier) that encapsulates one or more agents of interest (e.g., a detectable label such as a cancer imaging agent or an anti-cancer agent). Liposome is a vesicle comprised of one or more concentrically ordered lipid bilayers, which encapsulate an aqueous phase. The aqueous phase typically contains an agent to be delivered to a target site such as a tumor site. Upon reaching the target site, the liposome fuses with the plasma membranes of local cells to release the agent into the cytosol. Alternatively, the liposome is endocytosed or otherwise taken in by the cells as the content of a transport vesicle (e.g., an endosome or phagosome). Once in the transport vesicle, the liposome either degrades or fuses with the membrane of the vesicle and releases its contents. Liposome membranes can be constructed so that they become destabilized when the nearby environment becomes acidic (see, e.g., PNAS 84:7851, 1987; Biochemistry 28:908, 1989). Thus, when liposomes enter a target cell, they become destabilized and release their encapsulated contents. This destabilization process is termed fusogenesis. Dioleoylphosphatidylethanolamine (DOPE) is commonly used to facilitate this process.

A variety of methods are available for preparing liposomes. See, e.g., Szoka et al., Ann. Rev. Biophys. Bioeng. 9:467 (1980), U.S. Pat. Nos. 4,186,183, 4,217,344, 4,235,871, 4,261,975, 4,485,054, 4,501,728, 4,774,085, 4,837,028, 4,235,871, 4,261,975, 4,485,054, 4,501,728, 4,774,085, 4,837,028, 4,946,787, PCT Publication No. WO 91/17424, Deamer & Bangham, Biochim. Biophys. Acta 443:629-634 (1976); Fraley, et al., PNAS 76:3348-3352 (1979); Hope et al., Biochim. Biophys. Acta 812:55-65 (1985); Mayer et al., Biochim. Biophys. Acta 858:161-168 (1986); Williams et al., PNAS 85:242-246 (1988); Liposomes (Ostro (ed.), 1983, Chapter 1); Hope et al., Chem. Phys. Lip. 40:89 (1986); Gregoriadis, Liposome Technology (1984) and Lasic, Liposomes: from Physics to Applications (1993)). Suitable methods include, for example, sonication, extrusion, high pressure/homogenization, microfluidization, detergent dialysis, calcium-induced fusion of small liposome vehicles and ether fusion methods, all of which are well known in the art.

(Ii) Uses of Cancer-Targeting Peptides in Delivery of Anti-Cancer Agent or Imaging Agent to Cancer Cells In light of their ability of targeting cancer cells, any of the peptides described herein can be used for target delivery of an agent of interest (e.g., an anti-cancer agent or a detectable label such as an imaging agent) to cancer cells, thereby facilitating cancer treatment and/or diagnosis.

The delivery method described herein can be performed by contacting cancer cells or cells suspected of being cancerous a cancer-targeting peptide as described herein conjugated with the agent of interest. Cells suspected of being cancerous are cells that display one or more cancer cell characteristics, e.g., immortalization, loss of contact inhibitions, reduced cellular adhesion, invasiveness, loss of anchorage dependence, lower serum requirements, selective agglutination by lectins, molecular changes in cell membrane components, disorganization of the cytoskeleton, increase in negative surface charge of cell membrane, increased sugar transport, appearance of virus specific transplantation rejection antigens, defective electrical communication, increased secretion of proteolytic enzymes, aldolases, and increased rate of glycolysis. In some embodiments, the cancer-targeting peptide/agent conjugate is incubated with a sample having or suspected of having cancer cells. Such a sample can be a sample containing cultured cancer cells, a tissue sample obtained from a subject who has or is suspected of having cancer, or an in vivo tissue sample in such a subject (e.g., a human patient).

Alternatively, the conjugate can be administered to a subject who has or is suspected of having cancer. A subject having cancer can be identified by routine medical procedures. A subject suspected of having cancer may show one or more symptoms associated with certain types of cancers. Cancer symptoms vary, depending upon the types of cancers. Typical cancer symptoms include, but are not limited to, cough or blood-tinged saliva (lung cancer), a change in bowel habits such as continuous diarrhea or blood in stools (colon cancer), unexplained anemia (bowel cancers), breast lump or breast discharge (breast cancer), lumps in the testicles or enlarged testicles (cancer of the testicles), frequent urination or enlarged prostate gland (prostate cancer), and/or swollen lymph nodes (related to various cancers). Such subjects can be identified via routine medical procedures.

In some embodiments, a cancer-targeting peptide, conjugated with an anti-cancer agent or a detectable label as described herein, is mixed with a pharmaceutically acceptable carrier to form a pharmaceutical composition. The carrier in the pharmaceutical composition must be "acceptable" in the sense of being compatible with the active ingredient of the formulation (and preferably, capable of stabilizing it) and not deleterious to the subject to be treated. For example, solubilizing agents such as cyclodextrins, which form more soluble complexes with the anti-viral agents described herein, or more solubilizing agents, can be utilized as pharmaceutical carriers for delivery of the anti-viral agents. Examples of other carriers include colloidal silicon dioxide, magnesium stearate, sodium lauryl sulfate, and D&C Yellow #10. See, e.g., Remington's Pharmaceutical Sciences, Edition 16, Mack Publishing Co., Easton, Pa. (1980); and Goodman and Gilman's "The Pharmacological Basis of Therapeutics", Tenth Edition, Gilman, J. Hardman and L. Limbird, eds., McGraw-Hill Press, 155-173, 2001.

To deliver the anti-cancer agent or the detectable label to a target site, the composition described herein can be administered orally, parenterally, topically, rectally, nasally, buccally, vaginally, via an implanted reservoir, or via inhalation spray. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques.

A sterile injectable composition, e.g., a sterile injectable aqueous or oleaginous suspension, can be formulated according to techniques known in the art using suitable dispersing or wetting agents (such as Tween 80) or suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation.

A composition for oral administration can be any orally acceptable dosage form including, but not limited to, capsules, tablets, emulsions and aqueous suspensions, dispersions and solutions. In the case of tablets/capsules for oral use, carriers which are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. A nasal aerosol or inhalation composition can be prepared according to techniques well known in the art of pharmaceutical formulation. An oxadiazole compound-containing composition can also be administered in the form of suppositories for rectal administration.

A composition containing one or more of the cancer-targeting peptides described herein conjugated with an anti-cancer agent can be used in cancer treatment, particularly in treating GRP78-positive cancers. Cancer cells are cells having the capacity for autonomous growth, i.e., an abnormal state or condition characterized by rapidly proliferating cell growth. It is meant to include all types of cancerous growths or oncogenic processes, metastatic tissues or malignantly transformed cells, tissues, or organs, irrespective of histopathologic type or stage of invasiveness. The just-noted composition, containing an effective amount of the anti-cancer agent, can be administered to such a subject as described above. Optionally, a subject who carry GRP78-positive cancer cells can be first identified via routine methods, e.g., PCR or immunoassays, and then treated with the composition described herein.

Treating or treatment refers to the application or administration of a composition including one or more active agents to a subject, who has cancer, a symptom of cancer, or a predisposition toward cancer, with the purpose to cure, heal, alleviate, relieve, alter, remedy, ameliorate, improve, or affect cancer, the symptoms of cancer, or the predisposition toward cancer.

A composition containing one or more of the cancer-targeting peptides described herein conjugated with a detectable label such as an imaging agent can be used for detecting presence of cancer cells and/or cancerous tissues (e.g., cancer diagnosis and/or cancer imaging). When such a composition is used for in vivo tumor imaging, a suitable amount of the composition (e.g., containing about 20 μg of a cancer-targeting peptide and about 400 MBq of a radioactive molecule) can be injected to a suspected cancer patient, e.g., a patient carrying or suspected of carrying a solid tumor. The patient is then subjected to scintigraphy at suitable periods, e.g., 2 h, 4 h, 24 h, 48 h, and/or 72 h, after injection. Radioactivities of the whole body and the regions of interest are normalized against background activity and the presence/absence of tumor matter can be determined based on the results thus obtained.

The anti-cancer agent or the detectable label in the compositions described herein are administered in effective amounts. An "effective amount" is that amount of the anti-cancer agent or the detectable label that alone, or together with further doses, produces one or more desired responses, e.g. inhibit cancer cell growth, induce cancer cell apoptosis, or suppress cancer cell metastasis, or signal presence of cancer cells. In the case of treating a cancer, the desired responses include inhibiting the progression of the disease. This may involve only slowing the progression of the disease temporarily, although more preferably, it involves halting the progression of the disease permanently. This can be monitored by routine methods or can be monitored according to diagnostic methods of the invention discussed herein. The desired responses to treatment of the disease or condition also can be delaying the onset or even preventing the onset of the disease or condition.

Effective amounts will depend, of course, on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

(iii) Computational Methods for Identifying Cancer-Targeting Peptides

Practical software programs, including combinatorial construction of peptide-structure library (Buildpep), binding pocket analyzer (PscanMS), high accuracy protein-ligand scoring program (HotLig), or combinations thereof, can be utilized in the computational methods described herein to design optimized cancer targeting peptides, preferable using a known cancer-targeting peptide as a lead. Based on these programs, a strategy of structure-based optimization of peptides targeting cancer marker proteins in silico, as illustrated in FIG. 1 (using human GRP78 as an exemplary cancer marker protein), was developed to identify peptides that target GRP78. Briefly, the structures of a protein of interest (e.g., a cancer cell-surface protein) and peptide ligands are first modeled and energy-minimized. Then flexible docking is applied to produce the complexes of peptide-binding domain of the protein of interest with peptide ligands. The initial resulting complexes are then further energy-optimized followed by analyzing various molecular interactions using HotLig package to identify the key pharmacophore of protein-targeting motif. After repeated in silico screening from the peptide library, new peptides can be designed and examined to optimize the in vitro binding via Biacore analysis. The results were finally validated by in vitro binding with various cancer cells and in vivo tumor imaging and therapeutic studies in mice.

The computational methods described herein can include homologous modeling and molecular docking to predict structural features of a cancer-cell surface protein, particularly surface features of the protein, and binding interactions with peptides, PscanMS for detection of binding pockets and protein surface calculation, and HotLig for energy minimization and interaction scoring to identify or optimize peptides that are capable of binding to the cancer-cell surface protein. Preferably, a peptide known to bind to the cancer-surface protein is used as a lead peptide for molecular docking. A peptide structural library (e.g., a database with peptide sequences and 3D-structural information) is used for identifying and optimizing peptides targeting the cancer cell-surface protein. The overall schemes of these methods are exemplified in FIG. 2.

Structural modeling of a cancer-cell surface protein can be performed by computational tools known in the art, such as the method implemented in the PSIPRED server to predict Bryson et al., *Nucleic Acids Res.* 33:W36-38 (2005); and McGuffin et al., *Bioinformatics* 19:874-881 (2003). For example, homologs of the protein of interest can be identified from any publicly available databases, such as the protein data bank and their secondary structures/sequence alignment can be predicted/determined using the method provided in the PSIPRED server. The 3D structure of the protein of interest is then predicted by a conventional computational method, such as MODELLER 9v4 using functions of the AUTOMODEL class in python scripts with multiple-template mode. Eswar et al., Curr. Protoc. Bioinformatics, Chapter 5: Unit 5.6 (2006). The Discrete Optimized Protein Energy (DOPE) method also described in Eswar et al. can be used to select the best model from the 50 initially generated models. The loop regions of the energy-optimized model can then be refined by, e.g., the functions of LOOPMODEL class. Finally, the refined model can be subjected to energy minimization further by DEEPVIEW vers. 3.7 using the GROMOS 43B1 force field till the delta E between two steps dropped below 0.05 KJ/mol. Guex et al., Electrophoresis, 18:2714-2723 (1997).

Molecular docking of the protein of interest is then performed using, e.g. Modeller 9v4 as described above and a peptide structural library also noted above. The peptide structural library can be using Buildpep, which is a UNIX-shell script using the strategy that employs modeling and energy-minimization functions from the Modeller 9v4 package (Eswar et al.) to build a large pool of optimized 3D coordinates of peptide structures in combinatorial sequences with various lengths. The sequences of the peptides can be aligned to an alanine single amino acid template first and then energy-optimized peptides can be built by the AUTOMODEL functions of Modeller and the resulting library can be converted to a "mol2" file format by OpenBabel as described in Rajarshi et al., *J. Chem. Inf. Model.* 46:991-998 (2006).

The molecular flexible docking can then be performed by a method known in the art, such as the Dock 5.1 described in Kuntz, 1982. The Kollman partial charges (SYBYL 8.0, Tripos International, 1699 South Hanley Rd. St. Louis, Mo. 63144, USA) were applied to both protein and peptides for force field calculation. The parameters for Dock program can be set to iteratively generate 1,000 orientations and 200 conformers in binding pocket. The docked conformers can then be re-scored and ranked by HotLig to predict protein-ligand interactions, which is described below. The rendering of figures for molecular model can be performed by, e.g., Chimera (Lee et al., Cancer Res. 64:8002-8008; 2004).

Figure 10:
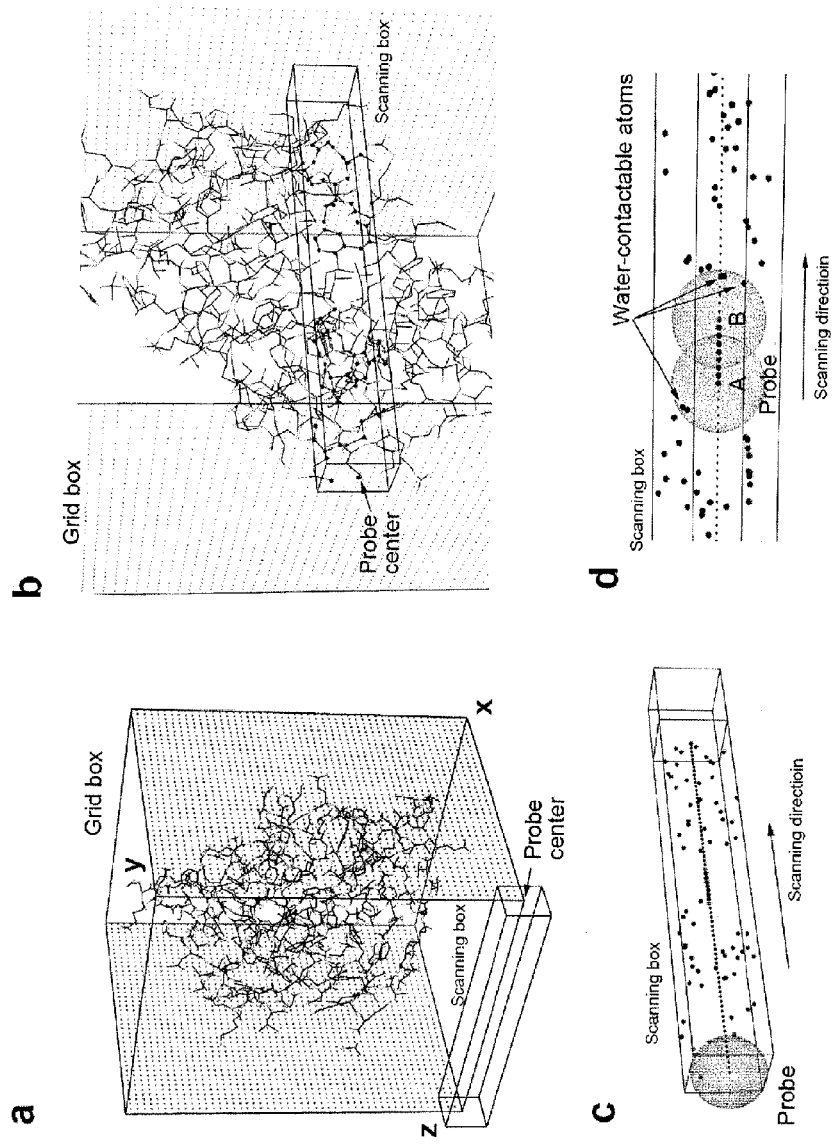
FIG. 10 is a diagram showing detection of binding pocket and water-contactable atoms by PscanMS for construction of a protein surface. Panel a: a diagram showing a grid box containing the region of a protein to be scanned can be set up for detection of binding cavities. Panel b: a diagram showing three-dimensional scanning. Panel c: a diagram showing the size of scanning box (r Å in radius, default is 3 Å). Panel d: a diagram showing positions contacted at least one atom of protein (positions A and B and position not contactable to any protein atoms.

In one example, binding pocket and water-contactable atoms can be detected by PscanMS to construct a protein surface. FIG. 10. A grid box containing the region of a protein to be scanned can be set up for detection of binding cavities. FIG. 10, panel a. To detect the cavity, the scanning box moves along the axes of the grid box and the probe scanned the scanning box once time every step the scanning box moved. All three dimensions can be scanned. FIG. 10, panel b. Once the protein atoms are found to be involved in the scanning box, the involved atoms were selected for detection of cavity. The size of scanning box can be set to fit the diameter of the probe (r Å in radius, default is 3 Å). FIG. 10, panel c. To detect the cavity inside the selected atoms involved in the scanning box, the probe moved along the scanning direction in a step length of dS Å is 0.5 Å). As shown in FIG. 10, panel d, the positions A and B, the probe contacted at least one atom of protein, but the positions that located between A and B are not contactable to any protein atoms. The protein atoms contacted by the probe at the A and B positions are defined as the "water-contactable atoms". The positions A and B are also defined as the "pocket dots" which can be used to illustrate the configuration of cavity. Additionally, the distance between one "pocket dot" and one water contactable atom of protein is in the range of (r−ds) to r Å. The minimum length of a space (between any two protein atoms) buried inside the protein can be detected is 2(r+dS)Å. Since the water contactable atoms are identified, the protein surface can thus be calculated using these surface atoms and their neighbor atoms by using their radii.

Figure 2:
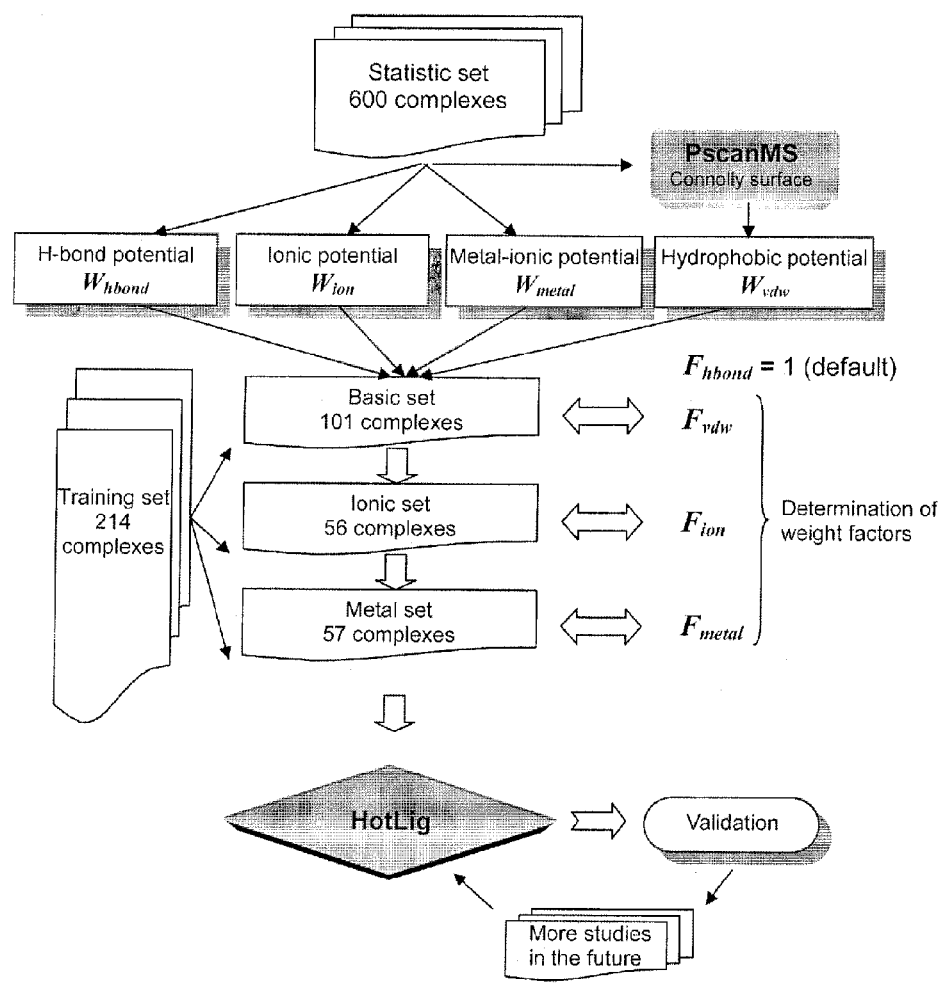
FIG. 2 is a schematic illustration of HotLig scoring function.
Figure 3:
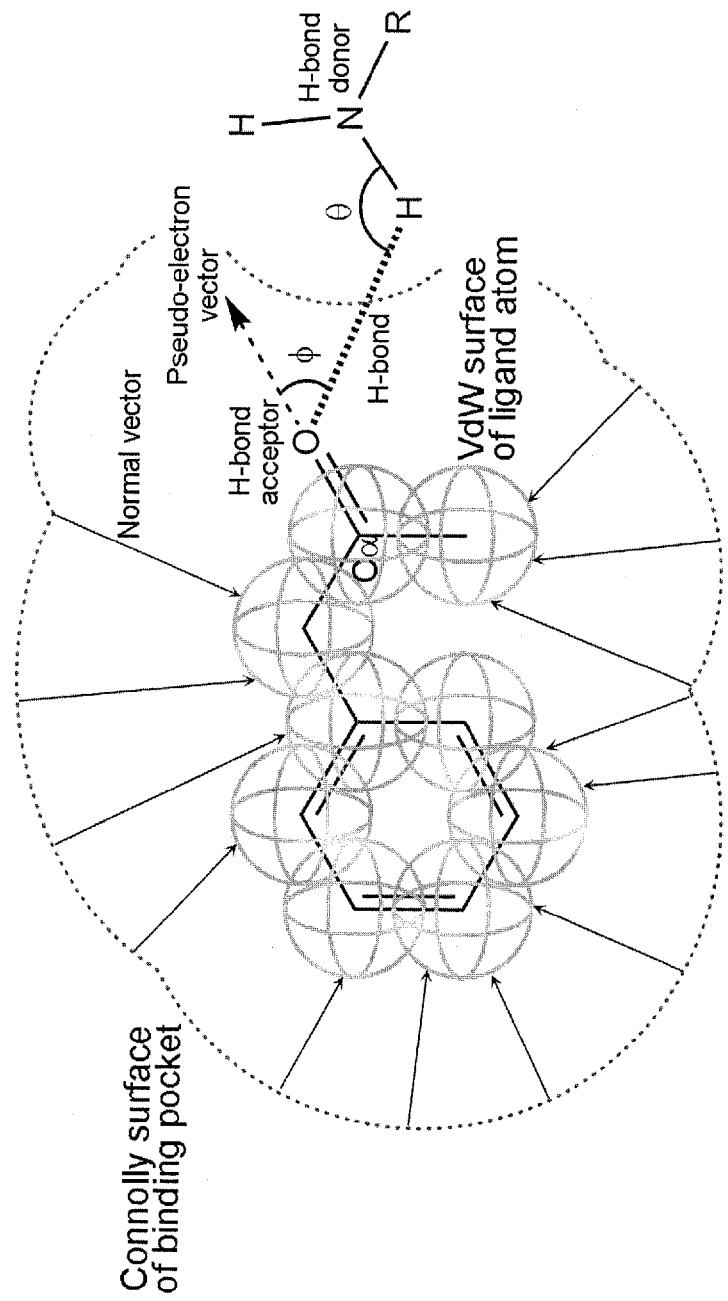
FIG. 3 is a schematic illustration of parametric analysis of protein-ligand interactions applied in HotLig.

HotLig is used in computational design/optimization of cancer-targeting peptides. HotLig is a knowledge-based and empirical-based scoring program for prediction of protein-ligand interactions. FIG. 2 illustrates the scheme of HotLig development. One of the innovative features in HotLig is the introduction of parameters for "intermolecular surface distance" into the distance-dependent functions for scoring various molecular interactions, such as polar interactions (hydrogen bonding, ionic interaction, metal-ion coordination) and non-polar interactions (hydrophobic effects). As illustrated in FIG. 3, in order to estimate the polar interactions quantitatively, the atomic surface distances can be calculated from the distance between centers of the two interactive atoms minus the summation of van der Waals radii. Hence, the HotLig excluded the differences of various atomic van der Waals radii, and assessed exactly how close the two interactive atoms were, when hydrogen bonding, ionic interaction or metal-ion coordination was formed.

As shown in FIG. 2, a statistic dataset (containing, e.g., 600 complexes) and a training set (containing, e.g., 214 complexes) from protein data bank (rcsb.org) can be used for the development of HotLig scoring functions. Examples of the statistic dataset and the training set are listed in Tables 1 and 2 below:

TABLE 1

Statistic set containing 600 complexes collected from PDB for the study of knowledge-based potential.

| | | | | | | | | | | | | | |
|---|---|---|---|---|---|---|---|---|---|---|---|---|---|
| 1a0j | 1a42 | 1a46 | 1a4k | 1a50 | 1a5g | 1a8i | 1a8t | 1a94 | 1aaq | 1abe | 1abf | 1acj | 1acl | 1acm |
| 1aco | 1adb | 1add | 1adf | 1aec | 1af2 | 1ah0 | 1ah3 | 1aha | 1aj7 | 1anf | 1apb | 1apt | 1apu | 1apv |
| 1apw | 1ase | 1ayx | 1azm | 1b05 | 1b0h | 1b1h | 1b2h | 1b32 | 1b3f | 1b3g | 1b3h | 1b3l | 1b40 | 1b46 |
| 1b4h | 1b4p | 1b4z | 1b51 | 1b52 | 1b58 | 1b5g | 1b5h | 1b5i | 1b5j | 1b6a | 1b6h | 1b7h | 1b9j | 1ba8 |
| 1baf | 1bai | 1bap | 1bb0 | 1bbz | 1bcu | 1bhf | 1bll | 1bn1 | 1bn3 | 1bn4 | 1bnm | 1bnn | 1bnq | 1bnt |
| 1bnu | 1bnv | 1bnw | 1bra | 1bxo | 1bxq | 1bzm | 1bzy | 1c1c | 1c5c | 1c8k | 1cbx | 1cil | 1cla | 1cnw |
| 1cnx | 1cny | 1coy | 1cps | 1cru | 1csc | 1ct8 | 1ctt | 1cx2 | 1d0c | 1d3d | 1d3p | 1d3q | 1d3t | 1dbb |
| 1dbj | 1dbk | 1dbm | 1dcy | 1dhf | 1did | 1die | 1dih | 1dr1 | 1drf | 1duv | 1dwb | 1dwc | 1dwd | 1dy3 |
| 1dyr | 1e1y | 1e2f | 1e66 | 1e7v | 1e8w | 1e96 | 1eap | 1ebg | 1ee2 | 1eed | 1efy | 1ejb | 1ela | 1elc |
| 1epb | 1epo | 1epp | 1eqc | 1eqg | 1eta | 1etr | 1ets | 1ett | 1ewl | 1exw | 1eyq | 1f2a | 1f74 | 1f8e |
| 1f9y | 1fbc | 1fbf | 1fbp | 1fe2 | 1ffq | 1fjs | 1fkb | 1fkf | 1fkg | 1fki | 1fl3 | 1fl6 | 1flr | 1fm7 |
| 1fmo | 1fq4 | 1fq5 | 1fq6 | 1fq8 | 1g1d | 1g27 | 1g45 | 1g46 | 1g48 | 1g4j | 1g4o | 1g52 | 1g53 | 1g54 |
| 1gaf | 1gg5 | 1ghb | 1gic | 1gj7 | 1glq | 1gz8 | 1h1i | 1h3a | 1hak | 1hb1 | 1hbv | 1hdc | 1hdy | 1hef |
| 1hew | 1hfs | 1hlk | 1hpv | 1hri | 1hsl | 1ht8 | 1htf | 1htg | 1hvi | 1hvj | 1hvk | 1hvl | 1hvr | 1hvs |
| 1hw8 | 1hw9 | 1hyt | 1hyx | 1hyy | 1i76 | 1i91 | 1i9m | 1i9n | 1i9o | 1i9p | 1i9q | 1icn | 1ida |
| 1if8 | 1igj | 1ij8 | 1ik3 | 1ikg | 1iki | 1inc | 1itu | 1ivd | 1ive | 1ix1 | 1iyl | 1j4r | 1jak | 1jcx |
| 1jet | 1jeu | 1jev | 1jk7 | 1jkx | 1jq3 | 1kel | 1kgj | 1ki8 | 1klk | 1kmv | 1kn2 | 1kn4 | 1kno | 1kqb |
| 1kvo | 1kz8 | 1l82 | 1l83 | 1l86 | 1l87 | 1ld8 | 1ldm | 1lgr | 1lic | 1llo | 1lnm | 1lpd | 1lrh | 1lri |
| 1lst | 1ly3 | 1lyb | 1m17 | 1m2x | 1m52 | 1m79 | 1m7y | 1mcb | 1mcf | 1mch | 1mcj | 1mcr | 1mcs | 1mdq |
| 1mdr | 1me8 | 1mfc | 1mfe | 1ml4 | 1mnc | 1moq | 1mrk | 1mrs | 1mup | 1nc1 | 1nhx | 1nis | 1njs | 1nms |
| 1nnb | 1nqu | 1nqx | 1o9f | 1odc | 1ogx | 1oiy | 1ooq | 1oq5 | 1ow2 | 1oyn | 1p4f | 1p6k | 1p6o | 1pa9 |
| 1pbd | 1pgp | 1pha | 1phd | 1phg | 1phh | 1pmq | 1pmv | 1pn9 | 1poc | 1ppc | 1pph | 1ppk | 1ppl | 1ppm |
| 1pso | 1q6z | 1q92 | 1qci | 1qhy | 1qka | 1qkb | 1ql7 | 1ql8 | 1qmg | 1qxy | 1rbp | 1rds | 1rgk | 1rgl |
| 1rne | 1rnt | 1rob | 1rpa | 1rus | 1s2a | 1s5s | 1sln | 1slt | 1snc | 1sre | 1srj | 1stp | 1t31 | 1t46 |
| 1t4e | 1tbb | 1tdb | 1tet | 1tha | 1the | 1thz | 1tka | 1tlp | 1tmn | 1tmt | 1tng | 1tnh | 1tni | 1tnj |
| 1tnk | 1tnl | 1tpp | 1tt8 | 1ttm | 1tu7 | 1tx2 | 1u0h | 1u1x | 1u2y | 1u32 | 1u4g | 1ulb | 1uof | 1us0 |
| 1uu3 | 1uwh | 1uwz | 1uzf | 1v2k | 1val | 1vam | 1vot | 1w82 | 1w96 | 1w9u | 1wb0 | 1wvm | 1x7r | 1x8b |
| 1xid | 1xie | 1xii | 1xli | 1xnk | 1xnz | 1xo2 | 1xoz | 1xpo | 1xuo | 1y57 | 1yda | 1ydb | 1ydd | 1yeg |
| 1yei | 1yej | 1yqy | 1yuh | 1yvm | 1yvx | 1ywn | 1yyy | 1zkl | 1zl2 | 1zos | 1zsb | 1zz3 | 1zzz | 2a1h |
| 2a3i | 2ab2 | 2ack | 2ada | 2ai2 | 2ai8 | 2aie | 2ak3 | 2akw | 2anj | 2ao0 | 2b0m | 2b7a | 2bb7 | 2bik |
| 2brc | 2bua | 2byi | 2bz6 | 2c1a | 2c4w | 2cbu | 2ccs | 2cgr | 2chl | 2cht | 2cpp | 2csc | 2ctc | 2cvd |
| 2dbl | 2dri | 2er0 | 2er6 | 2er7 | 2er9 | 2f4j | 2f7d | 2f8c | 2f94 | 2fda | 2fdd | 2fm0 | 2fm5 | 2fp7 |
| 2fq9 | 2fqr | 2g28 | 2gbp | 2gfs | 2gke | 2gss | 2h4n | 2ifb | 2ldb | 2mcp | 2msb | 2olb | 2pcp | 2phh |
| 2pk4 | 2plv | 2qwb | 2qwc | 2qwd | 2qwe | 2qwf | 2qwg | 2r04 | 2r07 | 2rnt | 2sim | 2sns | 2tmn | 2xim |
| 2xis | 2yhx | 2ypi | 35c8 | 3cla | 3cpa | 3csc | 3er3 | 3fx2 | 3gch | 3gpb | 3hvt | 3mth | 3pgm | 3ptb |
| 3tmn | 3tpi | 3ts1 | 43ca | 4aah | 4cla | 4cts | 4dfr | 4er1 | 4er2 | 4er4 | 4erk | 4est | 4fab | 4gr1 |
| 4hvp | 4mdh | 4pah | 4phv | 4sga | 4tim | 4tln | 4tmn | 4ts1 | 4xia | 5abp | 5acn | 5cna | 5enl | 5er2 |
| 5hvp | 5icd | 5ldh | 5p21 | 5p2p | 5pah | 5sga | 5std | 5tim | 5tln | 5tmn | 5xia | 6abp | 6acn | 6apr |
| 6cpa | 6enl | 6rnt | 6rsa | 6tim | 6tmn | 7abp | 7acn | 7cat | 7dfr | 7est | 7hvp | 7taa | 7tim | 7tln |
| 8a3h | 8abp | 8acn | 8atc | 8cpa | 8gch | 8hvp | 8icd | 8xia | 9aat | 9abp | 9hvp | 9icd | 9ldt | 9rub |

TABLE 2

Training set containing 214 complexes

Basic set (101 complexes)

| | | | | | | | | | | | | | |
|---|---|---|---|---|---|---|---|---|---|---|---|---|---|
| 1a50 | 1a8i | 1ah0 | 1ah3 | 1bxo | 1c1c | 1c8k | 1cx2 | 1d0c | 1dyr | 1e1y | 1e66 | 1e7v | 1e8w | 1efy |
| 1ewl | 1eyq | 1fm7 | 1fmo | 1gg5 | 1gz8 | 1h3a | 1ij8 | 1iki | 1iyl | 1j4r | 1kgj | 1ki8 | 1klk | 1kmv |
| 1kz8 | 1lnm | 1lpd | 1lri | 1ly3 | 1m17 | 1m52 | 1m79 | 1me8 | 1moq | 1nc1 | 1nhx | 1nqu | 1ogx | 1oiy |
| 1ooq | 1oyn | 1p4f | 1pmq | 1pmv | 1qci | 1s5s | 1t46 | 1t4e | 1tbb | 1tnj | 1tx2 | 1u0h | 1u2y | 1u32 |
| 1us0 | 1uu3 | 1uwh | 1v2k | 1vot | 1w82 | 1w96 | 1w9u | 1x7r | 1x8b | 1xnk | 1xo2 | 1xoz | 1xuo | 1y57 |
| 1yvx | 1ywn | 1zkl | 1zl2 | 1zos | 2a1h | 2a3i | 2ab2 | 2ao0 | 2b7a | 2bik | 2brc | 2byi | 2bz6 | 2c4w |
| 2ccs | 2chl | 2cvd | 2f4j | 2f7d | 2fdd | 2fm0 | 2gfs | 4erk | 5std | 8a3h | | | | |

Ionic set (56 complexes)

| | | | | | | | | | | | | | |
|---|---|---|---|---|---|---|---|---|---|---|---|---|---|
| 1a0j | 1ayx | 1b4p | 1dhf | 1duv | 1ejb | 1eqc | 1eqg | 1f74 | 1f8e | 1fe2 | 1ffq | 1fjs | 1gj7 | 1ht8 |
| 1hw8 | 1hw9 | 1ikg | 1ivd | 1jak | 1jcx | 1jk7 | 1jkx | 1jq3 | 1kqb | 1m7y | 1ml4 | 1njs | 1nms | 1nqx |
| 1p6k | 1pa9 | 1pn9 | 1q92 | 1t31 | 1thz | 1tnl | 1tt8 | 1tu7 | 1u1x | 1wb0 | 2ai2 | 2akw | 2anj | 2b0m |
| 2bua | 2c1a | 2cbu | 2fda | 2fp7 | 2fqr | 2gke | 2gss | 2qwd | 35c8 | 7taa | | | | |

TABLE 2-continued

Training set containing 214 complexes

Metal set (57 complexes)

| | | | | | | | | | | | | | | |
|---|---|---|---|---|---|---|---|---|---|---|---|---|---|---|
| 1a8t | 1b6a | 1bzy | 1cil | 1cru | 1ctt | 1dcy | 1dy3 | 1e2f | 1ee2 | 1f9y | 1g27 | 1h1i | 1hb1 | 1hfs |
| 1hlk | 1hy7 | 1i76 | 1ik3 | 1itu | 1ix1 | 1kvo | 1ld8 | 1lrh | 1m2x | 1mrs | 1oq5 | 1ow2 | 1p6o | 1q6z |
| 1qmg | 1qxy | 1s2a | 1sln | 1snc | 1ttm | 1u4g | 1uof | 1uwz | 1uzf | 1xii | 1xnz | 1xpp | 1yqy | 1yvm |
| 1zz3 | 2ai8 | 2aie | 2bb7 | 2cpp | 2f8c | 2f94 | 2fm5 | 2g28 | 4pah | 4tln | 5pah | | | |

* Three subsets were classified according to the molecular interactions between protein and ligand.

The principle of derivation of distance-dependant potential from the occurrence frequencies of paired atoms is similar to Velec's approach, which had been implemented in Drug-Score. In addition to analyzing molecular interactions based on "Sybyl-defined" atom types in previous studies (Velec, H. F. et al. *J. Med. Chem.* 48(20), 6296-303. (2005); SYBYL 8.0, Tripos International, 1699 South Hanley Rd., St. Louis, Mo., 63144, USA), HotLig can further analyze the pharmacophore of each atom for scoring molecular interactions. Additionally, the "atomic surface distance" can be used in the parametric functions of HotLig rather than the "atomic center distance". Briefly, the predicted binding potentials can be derived from the statistic set according to the occurrence frequencies of the paired pharmacophores in molecular interactions. Then, the weight factors for each binding potential can be determined via learning from the training set.

To give a quantitative score for a protein-ligand complex, the Connolly surface of protein can be first calculated by PscanMS, which detects binding cavity and 3D patterns of structural information and also calculates solvent-accessible surface and Connolly surface of proteins. The resulting surface features can be outputted as dot surface in QCPE-compatible MS format (Connolly, 1983), which possesses a sectioned area value and a unit normal vector for each dot. The molecular interactions can then be analyzed and divided into polar- and non-polar-interactions according to their pharmacophore classifications. Polar interactions include hydrogen bonding, ionic interaction, and metal-ion coordination; whereas non-polar interactions include hydrophobic interactions (which may not distinguishable from van der Waals interactions in HotLig) that occurred on carbon-carbon contacts.

Figure 7:
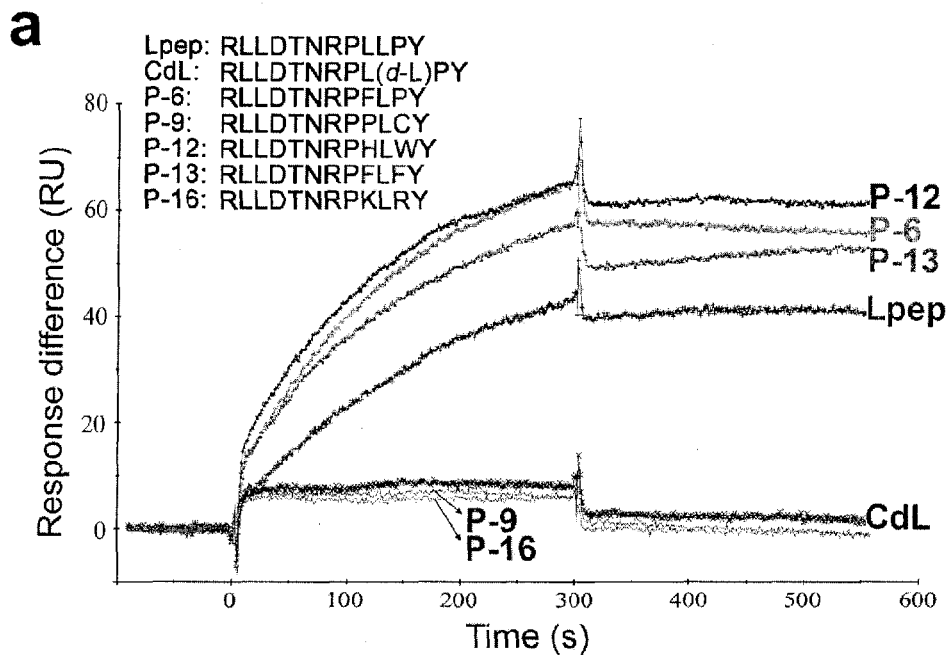
FIG. 7 is a diagram showing in vitro binding evaluation of cancer-targeting peptides. a: A representative Biacore sensorgram of 50 µM peptides binding to the full-length recombinant GRP78. Peptide CdL was used as a negative control. b: Binding of FITC-labeled peptides to breast cancer cell line, MDA-MB-231 and NPC TW01 by flow cytometry. c: Binding of FITC-labeled peptides to primary human breast cancer, BC0145 and BC0244 engrafted in NOD/SCID mice. d: Binding of FITC-labeled peptides to clinical breast cancer specimens, BC0854 and BC0861 by flow cytometry.
Figure 7:
Figure 7:
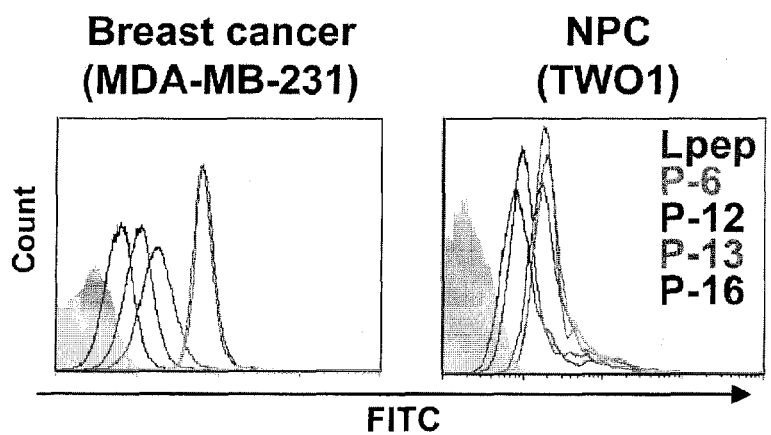
Figure 7:
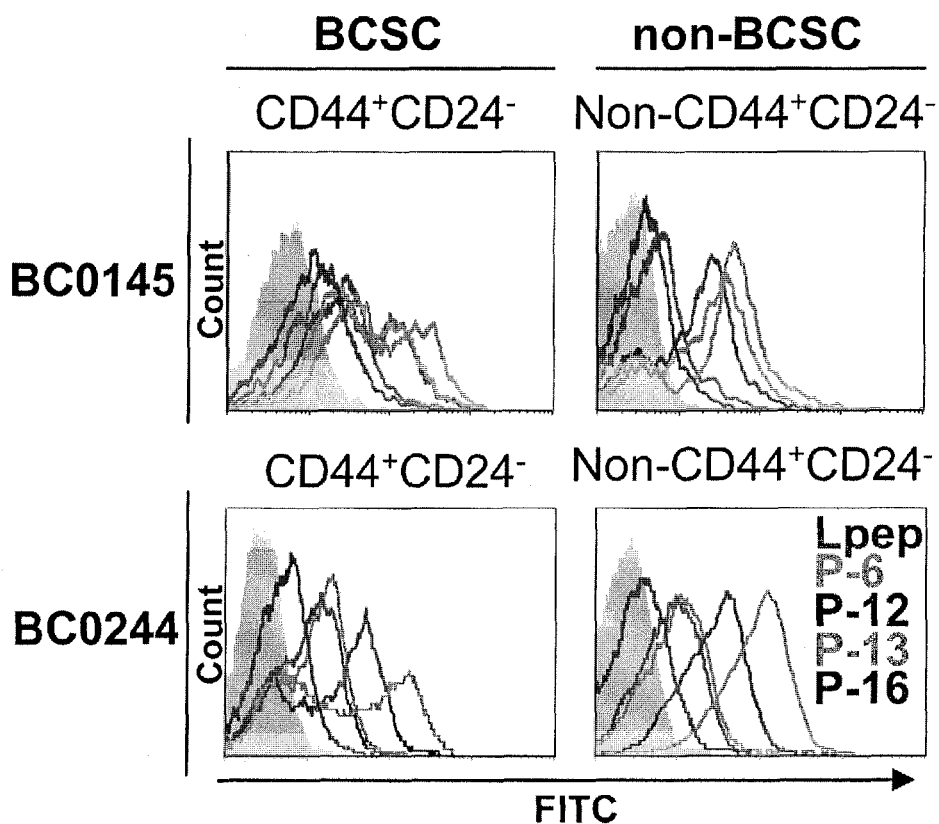
Figure 7:
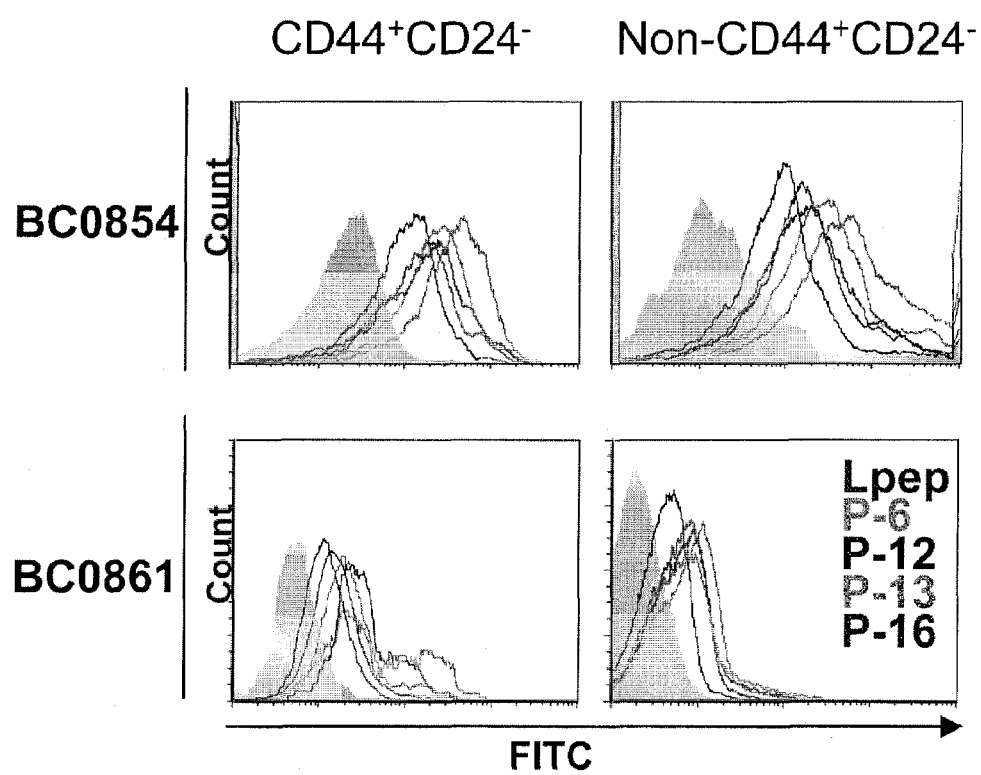

To assess the energy potentials of polar interactions, the distance-dependent scoring functions can be derived from fitting the normalized distribution of atomic surface distance (δ atomic surface distance between atoms N & O in FIG. 3) vs. angle donor-H-acceptor (θ) and angle electron-acceptor-H (φ) that were measured from the paired pharmacophores (FIG. 7). The potential for non-polar interaction can be derived from fitting the distribution of normal vector length (v) between Connolly protein surface and ligand atomic surface (FIG. 3). Additionally, the integration of the contacted area (A) on Connolly surface can also be introduced in the calculation of non-polar potential.

The potential of hydrophobic interaction can be derived from the normalized distribution of the length of ligand-contacted normal vector (v) between the protein Connolly surface and ligand atomic surface. Additionally, the sectioned area (A) associated with the normal vector on Connolly surface can be introduced into the calculation of non-polar potential. The final equation for scoring of hydrophobic interaction ($\Delta E_{vdw}$) can be:

$$\Delta E_{vdw} = A \times W_{vdw}(v)$$

Overall, combining the equations of each kind of interaction, the resulting parametric equation for the binding energy ($\Delta E$) between a protein (p) and a ligand (l) is represented as:

$$\begin{aligned}\Delta E_{p,l} &= \Delta E_{polar}(\delta, \theta, \phi) + \Delta E_{non\text{-}polar}(v, A) \qquad , (\phi < 100°). \\ &= F_{hbond} \times \sum_{h}(\cos(180° - \theta_h) \times W_{hbond}(\delta_h)) + \\ &\quad F_{ion} \times \sum_{i} W_{ion}(\delta_i) + F_{metal} \times \sum_{m} W_{metal}(\delta_m) + \\ &\quad F_{vdw} \times \sum_{v}(A_v \times W_{vdw}(v_v))\end{aligned}$$

Here, h refers to the pair of H-bond; i refers to the pair of ionic interaction; m refers to the pair of metal-ion coordination and v refers to the ligand-contacted normal vector in hydrophobic interaction.

Figure 6:
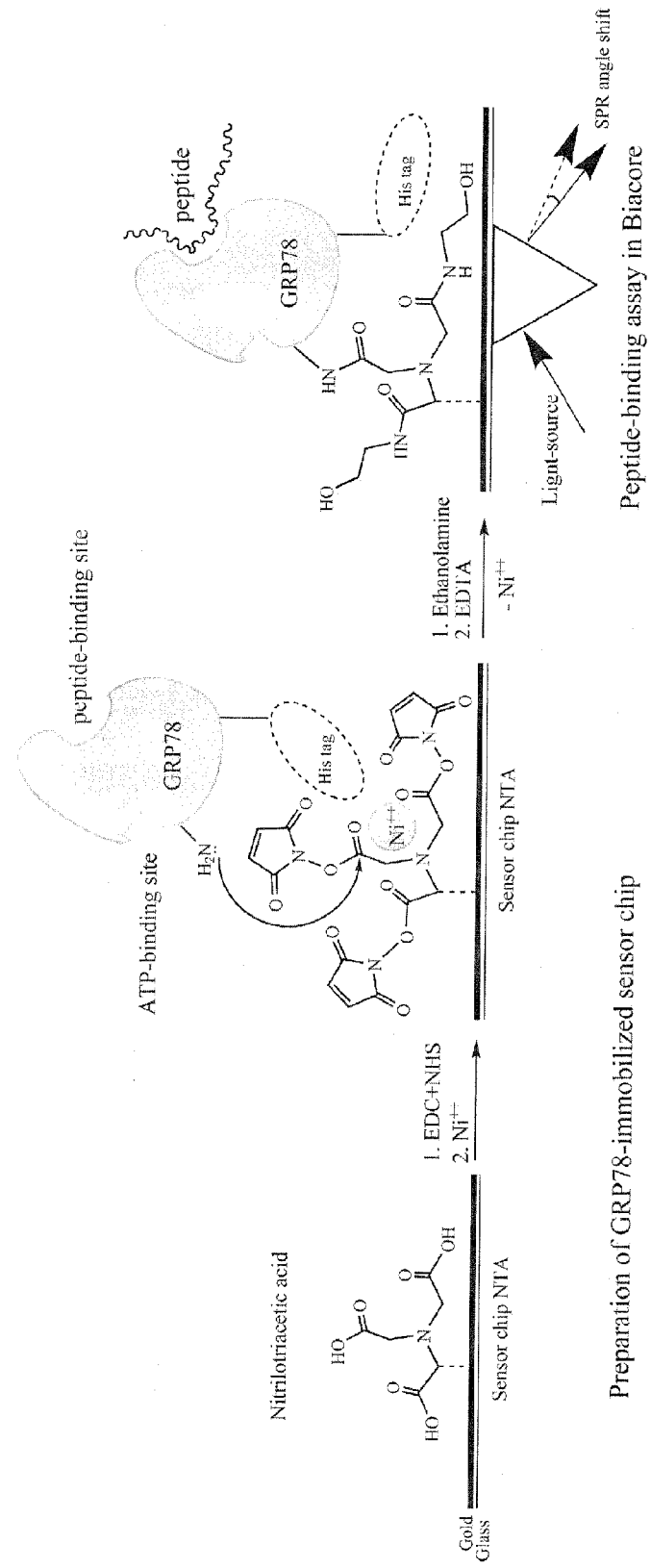
FIG. 6 is a diagram showing oriented immobilization of protein GRP78 on sensor chip NTA.

To optimize the weight factor for each kind of interaction, the $F_{hbond}$ can be set as 1 and then the other factors, $F_{vdw}$, $F_{ion}$, $F_{metal}$, can be determined from the training set as illustrated in FIG. 6. This training set can be classified into three subsets: a basic set, an ionic set, and a metal set. See, e.g., FIG. 2. The interactions between a protein and its cognate ligands can be analyzed for the classification. In the basic set, neither charged ionic interaction nor metal coordination is contained in the interactions between the protein and ligand in the complex (FIG. 2). The complexes which possess ionic interactions between a protein and its ligand without any binding through metal ion are assigned to the ionic set (FIG. 2). The metal set includes complexes, in each of which the protein binds to its ligand through metal coordination (FIG. 2). The weight factor $F_{vdw}$ can be first optimized based on the maximum success rate of prediction for the basic set while the $F_{hbond}$ is set as 1. Once the factor $F_{vdw}$ is determined, the optimal factor $F_{ion}$ can be determined through the iterative analysis of the ionic set. Similarly, the factor $F_{metal}$ can be obtained from the analysis of the metal set (FIG. 2).

The peptides targeting the cancer cell-surface protein of interest identified from or optimized by the computational methods described herein can then be tested in an in vitro assay (e.g., in vitro binding assay) or in vivo assay (e.g., in vivo imaging assay) to verify their activities of targeting cancer cells expressing the surface protein of interest.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLE 1

Computational Design of Cancer-Targeting Peptides

A series of novel cancer-targeting peptides was developed based on molecular modeling of GRP78 and in silico molecular docking and scoring using HotLig and L-peptide (Lee et al., 2004). L-peptide has the amino acid sequence of RLL-DTNRPLLPY (SEQ ID NO: 13). See U.S. Pat. No. 7,238,665.

(i) Determining Structural Features of Human GRP78

To design and optimize cancer-targeting peptides, homologous modeling and molecular docking were performed to characterize the structural features of human GRP78.

The method implemented in the PSIPRED server (Bryson et al. *Nucleic Acids Res.* 33: W36-38; 2005; and McGuffin et al. *Bioinformatics* 19: 874-881; 2003) was used for predicting the secondary structures and making sequence alignments. Initially, the structural information of GRP78 homolog (Protein Data Bank code: 2QWL, 1YUW, 2V7Y, 2OP6, 1DLX and 1U00) was used as the modeling templates. The 3D structure of GRP78 was constructed by MODELLER 9v4 (Eswar et al. *Curr. Protoc. Bioinformatics,* Chapter 5: Unit 5.6; 2006)) using functions of the AUTOMODEL class in python scripts with a multiple-template mode. The Discrete Optimized Protein Energy (DOPE) method (Eswar, et al.) was used to select the best model from the 50 initially generated models. The loop regions of the energy-optimized model were then refined by the functions of LOOPMODEL class. Finally, the refined model was subjected to energy minimization further by DEEPVIEW vers. 3.7 (Guex et al. *Electrophoresis,* 18:2714-2723; 1997) using the GROMOS 43B1 force field till the delta E between two steps dropped below 0.05 KJ/mol.

Next, the structure of human GRP78 was modeled using Modeller 9v4 as described above and the peptide structural library was constructed using Buildpep also described above. The molecular flexible docking was then performed by Dock 5.1 as described in Kuntz et al., *J. Mol. Biol.* 161:269-288 (1982). The Kollman partial charges were applied to both protein and peptides for force field calculation. The parameters for Dock program were set to iteratively generate 1,000 orientations and 200 conformers in binding pocket. The docked conformers were then re-scored and ranked by HotLig to predict protein-ligand interactions. The rendering of figures for molecular model was performed by Chimera (Kuntz, 1982; and Pettersen et al. *J. Comput. Chem.* 25:1605-1612; 2004).

Figure 4:
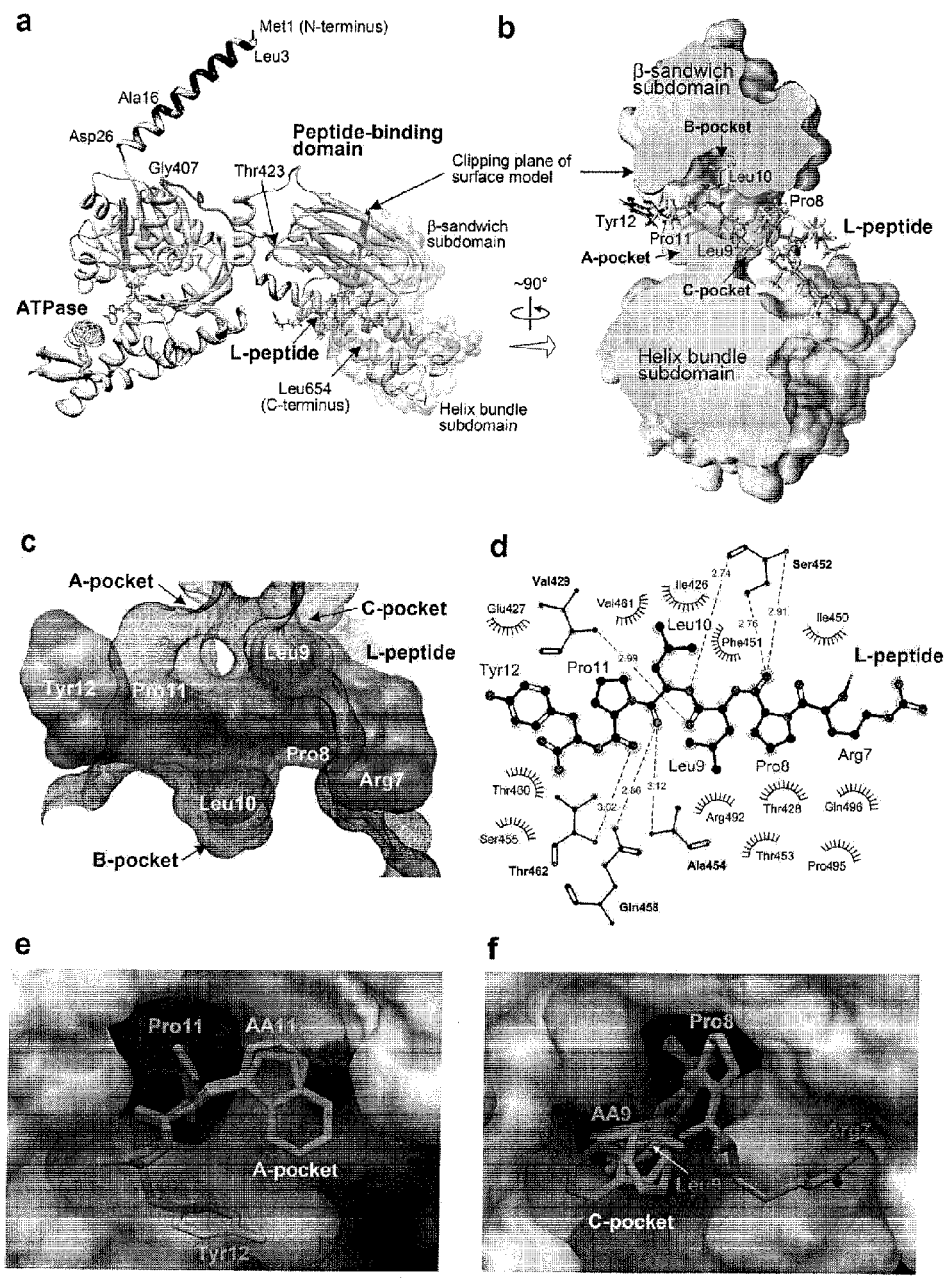
FIG. 4 is a diagram showing modeling of the 3D structure of human GRP78, a cancer marker protein, and optimization of peptides targeting human GRP78 using the L-peptide as a lead. a: modeling of human GRP78 shows that this protein is composed of a peptide-binding domain and an ATPase domain linked by a loop. b: the L-peptide binding site appears as a "tunnel" through which a binding peptide can pass. The peptide-binding site of the L-peptide is illustrated with identification of the A-, B-, and C-pockets, which are predicted to interact with Pro11, Leu10, and Leu9 of the L-peptide. c: The Connolly protein surface generated by PscanMS displays the perspective shape of the peptide-binding site and the geometric matching of the peptide molecule with the binding site. Pockets A and C are key sites for optimization of cancer-targeting peptides. d: Intermolecular hydrogen bonds between GRP78 and the L-peptide. Hydrogen bonds mainly occurred at the Pro8-Leu9-Leu10-Pro11 sequence of the L-peptide. e: The Trp and Phe amino acids were observed to be promising candidates for alterations at Pro 11 to fit in the A-pocket in different orientations because of their rigid, planar side chains. f: The C-pocket for Leu9 of the L-peptide could be replaced by many other amino acids which resulted in similar orientations.

The structure of human GRP78 thus modeled is shown in FIG. 4, panel a. This protein was found to contain two major structural domains, a peptide-binding domain and an ATPase domain. This structural model with respect to the ATPase domain is consistent with the an X-ray crystallography determination as described in Wisniewska et al., PLoS One 5:e8625 (2010) and Connolly, Science 221:709-713; 1983. The value of the root-mean-square deviation was as low as low as 0.6 Å, when compared with the modeled ATPase domain with the crystallographic data via structural superimposition. In the model, the peptide-binding domain was found to be composed of a β-sandwich subdomain and a helix-bundle subdomain (FIG. 4, panel a). The β-sandwich subdomain is made up by two layers of β-sheets stacked together, followed by several tandem helices. These helices are further folded to form the helix-bundle subdomain at the C-terminus. On the other hand, the sequence from Met1 to Asp26 at the N-terminus of GRP78 was predicted to have a single helix. Since the GRP78 protein moves to the surface in cancer cells, the hydrophobicity of this N-terminal helix was also investigated according to the attributes of its amino acids. A hydrophobic region (Leu3 to Ala16) was identified within the helix (FIG. 4, panel a).

(ii) Novel Surface-Directed Algorithm for Scoring Protein Peptide Interactions

Software HotLig (described above) was developed for structure-based optimization of peptides capable of binding to human GRP78.

Figure 5:
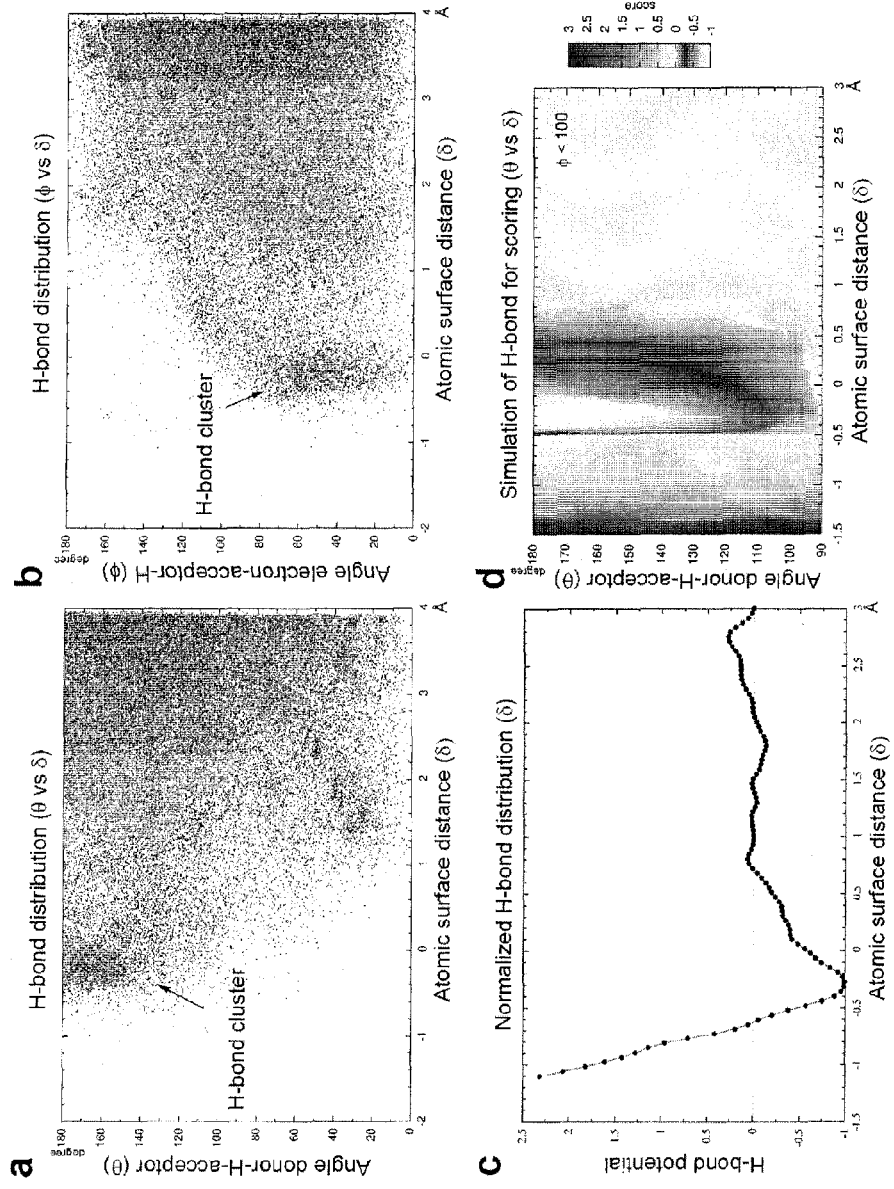
FIG. 5 is a diagram showing derivation of H-bond potential from the statistic distribution of H-bond parameters. a: The distribution of angle donor-H-acceptor ($\theta$) vs. atomic surface distance ($\delta$) of H-bonding pairs shows the atomic distance is smaller then the summation of radii of H-bond donor and acceptor atoms ($\delta$<0) when H-bond occurred. The H-bond cluster also indicated that the optimal angle of $\theta$ is 180 degree and the binding force is decreasing with the smaller angle of $\theta$. b: The distribution of the H-bond cluster is not significantly correlate with the angle electron-acceptor-H $\phi$. Generally, the angles $\phi$ were smaller than 100 degree in H-bond cluster. c: The distance-dependant potential for H-bond ($W_{hbond}$) was derived from (a) using the normalization method as Velec's approach (Velec et al., 2005) d: To simulate the H-bond potential from the distribution of H-bond cluster, the angle $\theta$ and $\phi$ were introduced in HotLig to calculate the energy score of H-bond ($\Delta E_{hbond}$) as the following equation: $\Delta E_{hbond}$=cos $(180-\theta) \times W_{hbond}(\delta)$, $\phi$<100
Figure 9:
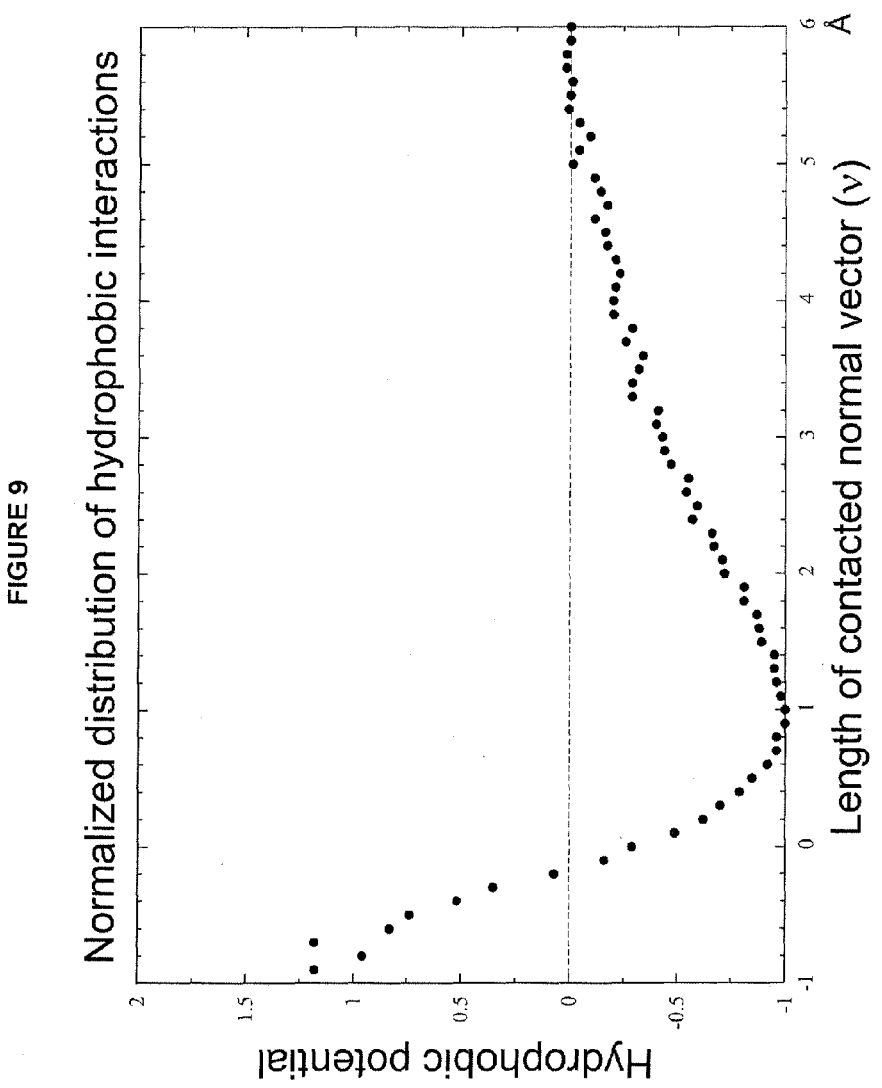
FIG. 9 is a chart showing normalized distribution of hydrophobic interactions.

The scheme for the development of HotLig algorithm was shown in FIG. 2 also described above. HotLig is a knowledge-based and empirical-based scoring program with outstanding predictive power for protein-ligand interactions. The statistical distribution and the derived function for the simulation of hydrogen-bonding pairs versus the atomic surface distance were shown in FIG. 5. For the estimation of the hydrophobic interactions, the Connolly surface of protein (Connolly, Science 221:709-713; 1983), which was composed of surface-point coordinates, areas, and normal vectors, was applied in the calculation of intermolecular surface distance and the contact area. FIG. 7. The normal vectors were the vectors perpendicular to the protein surface, pointing toward the ligand side. Hundreds of thousands of normal vectors on Connolly surface of protein were involved in the calculation of molecular surface contact. The measured intermolecular surface distance and contact area were then used to estimate the contribution of hydrophobic contact. FIG. 9. The potential for hydrophobic interaction was derived from fitting the normalized distribution of the length (v) of contacted normal vector between Connolly protein surface and ligand atomic surface. Additionally, the integration of contacted area (A) on Connolly surface was also introduced in calculation of non-polar potential. The final equation for scoring of hydrophobic interaction ($\Delta E_{vdw}$) is: $\Delta E_{vdw} = A \times W_{vdw}(v)$.

As shown in Table 3 below, the HotLig improved the docking accuracy of the software Dock v5.1 from 44.39% to 71.96% when re-scored the docked results generated by Dock. In addition, if the experimental coordinates of cognate ligands were also included for scoring, the success rate of the HotLig could reach 88.32%. Table 3. Similar results were also observed when validation was performed using the Gold dataset (Jones et al., J. Mol. Biol. 267:727-748; 1997). See Table 3.

TABLE 3

Re-scoring of docked conformers by the HotLig improved the accuracy of prediction significantly[a].

| Dataset | Dock v5.1 success rate (%) | HotLig success rate (%) | |
|---|---|---|---|
| | | native ligand pose excluded | native ligand pose included |
| HotLig training set (214 complexes) | 44.39 | 71.96 | 88.32 |
| Gold dataset (100 complexes) | 35 | 69 | 87 |

[a]The success rate were calculated at the criteria of RMSD ≤2.0 Å (comparing with the native pose of cognate ligand). The native pose refers to the experimental coordinates of binding conformation of the cognate ligand.

Furthermore, utilizing another Wang's dataset (Wang et al., J. Med. Chem. 46:2287-2303; 2003), the success rate of binding mode prediction of the HotLig was as high as 91%, when comparing with many other known scoring programs and HotLig was the best program in the list. See Table 4 below:

TABLE 4

Comparing prediction accuracy for binding mode by HotLig with 11 other scoring programs using Wang's dataset[3].

| scoring function[a] | Success rate (%) | | | | |
|---|---|---|---|---|---|
| | RMSD ≤1.0 Å | RMSD ≤1.5 Å | RMSD ≤2.0 Å | RMSD ≤2.5 Å | RMSD ≤3.0 Å |
| HotLig | 79 | 87 | 91 | 93 | 94 |
| Cerius2/PLP | 63 | 1.69 | 76 | 79 | 80 |
| SYBYL/F-Score | 56 | 66 | 74 | 77 | 77 |
| Cerius2/LigScore | 64 | 68 | 74 | 75 | 76 |
| DrugScore | 63 | 68 | 72 | 74 | 74 |
| Cerius2/LUDI | 43 | 55 | 67 | 67 | 67 |
| X-Score | 37 | 54 | 66 | 72 | 74 |
| AutoDock | 34 | 52 | 62 | 68 | 72 |
| Cerius2/PMF | 40 | 46 | 52 | 54 | 57 |
| SYBYL/G-Score | 24 | 32 | 42 | 49 | 56 |
| SYBYL/ChemScore | 12 | 26 | 35 | 37 | 40 |
| SYBYL/D-Score | 8 | 16 | 26 | 30 | 41 |

[a]Scoring functions are ranked by their success rates at RMSD ≤2.0 Å (comparing with the native pose of cognate ligand).

To estimate the accuracy of HotLig in prediction of binding-affinity, the Wang's dataset was also used for evaluation. As shown in Table 5, the Rs value of the HotLig was 0.609, which was also better than most programs.

TABLE 5

Comparing prediction accuracy for binding affinity by HotLig with 11 other scoring programs using Wang's dataset

| Scoring functions | Spearman correlation coefficient (Rs) based on | |
|---|---|---|
| | the experimentally observed conformations | the best-scored conformations |
| X-Score | 0.660 | 0.698 |
| HotLig | 2.0.609 | 0.606 |
| Cerius2/PLP | 0.592 | 0.607 |
| DrugScore | 0.587 | 0.601 |
| SYBYL/G-Score | 0.569 | 0.531 |
| SYBYL/D-Score | 0.475 | 0.488 |
| SYBYL/ChemScore | 0.431 | 0.435 |
| Cerius2/LUDI | 0.430 | 0.456 |
| Cerius2/PMF | 0.369 | 0.367 |
| Cerius2/LigScore | 0.363 | 0.418 |
| SYBYL/F-Score | 0.283 | 0.253 |
| AutoDock | 0.141 | 0.423 |

Taken together, the software HotLig provides a novel surface-directed algorithm and exhibits excellent predictive power for protein-ligand interactions.

(iii) Design of Optimized Cancer-Targeting Peptides

The L-peptide, binding to GRP78 in a dose-dependent manner with a dissociation constant ($K_D$) of about 1~10 μM, was used as a lead peptide in this study.

To delineate the binding motif of the L-peptide and its detailed molecular interactions with GRP78, molecular docking, energy minimization, and interaction scoring were performed as outlined in FIG. 1. It was found that the L-peptide accessed a binding site at the center of the peptide-binding domain of GRP78. See FIG. 4, panel a. To depict the features of the L-peptide binding site hidden inside GRP78, a surface model of the peptide-binding domain was sliced open and shown by clipping a plane along the binding site. FIG. 1b shows that the L-peptide-binding site runs through the inter-region of the β-sandwich and helix-bundle subdomains, which appears as a "tunnel" for access of the L-peptide chain.

To illustrate GRP78-L-peptide interactions, three specific binding regions, A-, B- and C-pockets were identified in GRP78, which interacted, respectively, with Pro 11, Leu 10, and Leu9 of the L-peptide FIG. 4, panel b. As shown in FIG. 4, panel c, the Connolly surface represents the water-contactable surface of the protein (Connolly, 1983) and is shown as a dotted surface to display the perspective configuration of the peptide-binding site in GRP78. The surface structure of amino acids, Arg7-Pro8-Leu9-Leu10-Pro11-Tyr12 (RPLLPY), of the L-peptide showed a geometric matching of the peptide molecule binding site in GRP78. FIG. 1c. Obviously, these pockets provided a matched configuration, which allowed the RPLLPY sequence of the L-peptide to fit inside the peptide-binding pocket in GRP78.

A schematic diagram was constructed to represent molecular interactions between the L-peptide and GRP78. FIG. 4, panel d. The sequence, RPLLPY, interacted with the peptide-binding domain of GRP78 through hydrogen bonding with the L-peptide backbone, and hydrophobic contacts via side chains of the L-peptide. The hydrogen bonds mainly occurred at the PLLP peptide sequence of the L-peptide (FIG. 4, panel d). Since Val429, Ser452, Ala454, Gln458, and Thr462 of the GRP78 formed intermolecular hydrogen bonding with L-peptide (FIG. 1d); these amino acids play important roles in trapping peptide ligands for GRP78. Furthermore, the side chain of Leu10 of the L-peptide was found to contact with Val461, Ile426, and Phe451 of GRP78 (the radiating semi-circles in FIG. 1d) to form hydrophobic interactions. In contrast, except for amino acids at the 8th to 11th positions, other amino acids in the L-peptide sequence did not display significantly specific interactions with GRP78. Thus, the most significant binding sequence of the L-peptide to be docked in the peptide-binding domain of GRP78 was determined to consist of the PLLP sequence.

Practical software programs, including combinatorial construction of peptide-structure library (Buildpep), binding pocket analyzer (PscanMS) and high accuracy protein-ligand scoring program (HotLig) as described above, were utilized to design optimized cancer targeting peptides, using the L-peptide as a lead. Based on these programs, a strategy of structure-based optimization of cancer targeting peptides in silico, as illustrated in FIG. 1, was developed to identify peptides that target GRP78, using the L-peptide as a lead.

To improve binding affinity, structural modification was first focused on alterations of amino acids within the binding sequence of PLLP of the L-peptide (see discussions above). It is noted that the binding pockets A and C in GRP78 for Pro11 and Leu9, respectively, represent wide open grooves, suggesting that these two amino acids of the L-peptide are likely to be substituted during optimization. On the other hand, Leu10 of the L-peptide was invariable because of its limited and specific binding in the B-pocket (FIG. 4, panel c). Additionally, Pro8 was found to interact with GRP78 as a rigid amino acid which prevents folding to form a secondary helix structure of peptides. Therefore, Pro8 might also be conserved during optimization of the peptide sequence.

Thus, in order to optimize the binding sequence based on the structural features of pockets A and C in GRP78 as described above, Leu9 and Pro11 of the L-peptide were chosen for substitutions with different amino acids. As a result, a structural library of 400 peptides was built by changing Leu9 and Pro11 for in silico screening analysis. To prevent time-consuming docking procedures, the lengths of the peptides in the library were reduced to 6-mer peptides, i.e., RPXLXY. Flexible molecular docking was performed, and the molecular interactions were then estimated and predicted by HotLig as described above.

After docking various peptides in the library, Trp and Phe (i.e. AA11 in FIG. 4, panel e) with large planar side chains were observed to be the most promising candidates for substitution for Pro 11 of the L-peptide, because any of these substitutions could fit into the additional cavity of A-pocket, in addition to the Pro 11 binding site. On the other hand, the C-pocket for Leu9 binding of the L-peptide could be replaced by many other amino acids while preserving a similar matched configuration at C-pocket (FIG. 4, panel f). In addition, in consideration of the binding energy predicted by HotLig, there were 17 peptide candidates (P-1 to P-17 in Table 6 below) which exhibited low HotLig energy scores and thus represented good interactions of these peptide analogs with GRP78.

To further improve the diversity of peptide-candidate selection, another 9 peptides (PA-1 to PA-6 and PB-1 to PB-3 in Table 6) below were also included for comparison. For example, PA-1 contained hydrophobic Trp9 which was comparable to P-6 and the L-peptide because of the different-sized substitutions at the same 9th position of these peptides. In addition, PA-2 and PA-3 were substituted with negatively charged residues (Glu9 and Asp9, respectively), and PA-6 was altered with a positive charged His9 at the same position. Additionally, PA-4 and PA-5 had the substitution of two polar amino acids (Asn9 and Gln9), respectively, which acted as either an H-bond donor or acceptor; PB-1 and PB-2 increased the hydrophobicity by replacing the His9 of P-12. Furthermore, peptide PB-3 was modified with the amidation ($CONH_2$) to shield the negative charge of the COOH group.

Thus the structure-activity relationships of these designed GRP78-targeting peptides were validated by an in vitro binding assay and in vivo imaging assays as described in Example 3 below.

EXAMPLE 2

Preparation of Liposomes Conjugated with Cancer-Targeting Peptides

The cancer-targeting peptides can be conjugated with liposomes, which encapsulate one or more anti-cancer agents, one or more cancer imaging agents, or both following routine methods. See, e.g., Chen et al., *Anticancer Research* 30:65-72, 2010.

(i) Preparation of Liposomes

Liposomes were provided by Taiwan Liposome Co. Briefly, liposomes composed of distearoylphosphatidylcholine, cholesterol, and PEG-DSPE were hydrated at 55° C. in ammonium sulfate solution [250 mmol/L $(NH4)_2SO_4$ (pH 5.0) and 530 mOs] and extruded through polycarbonate membrane filters (Costar, Cambridge, Mass.) of 0.1- and 0.05-μm pore size with high-pressure extrusion equipment at 60° C. The final concentration of liposomes was determined by phosphate assay. Vesicle size was measured by dynamic laser scattering with a submicron particle analyzer. After preparation, the liposomes usually had a particle size ranging from 65 to 75 nm in diameter.

(ii) Preparation of Peptide Linked PEGylated Liposomes

The procedures for preparation of peptide linked liposome were adopted from the methods published previously. (Lee, T. Y., et al. *Cancer Res.* 64, 8002-8008. (2004)). A peptide was coupled to NHS-PEG-DSPE [N-hydroxysuccinimido-carboxyl-PEG (MW, 3400)-derived distearoylphosphatidylethanolamine (DSPE) (NOF Corporation, Tokyo, Japan)] at a 1:1.5 molar ratio. This coupling was performed with the unique free amine group in the NH2 terminus of the peptide to produce peptidyl-PEG-DSPE. The reaction was completed and confirmed by quantitation of the remaining amino groups. The amino group was measured with trinitrobenzenesulfonate reagent. The same method was used to prepare a control peptide to replace the cancer-targeting peptides and couple to NHS-PEG-DSPE for comparison. Peptidyl-PEG-DSPE was then conjugated to pre-formed liposomes encapsulating doxorubicin after co-incubation at temperature above the transition temperature of lipid bilayer. There were 300 to 500 molecules of the peptide per liposome, as determined by the method described in Kirpotin et al., Biochemistry 36:66-75, 1997.

(iii) Preparation of Peptide-$^{188}$Re-Labeled Pegylated Liposomes

The peptide-pegylated-lipopsomes (1 ml) was added to the $^{188}$Re (50-250 MBq) solution and incubation at 60° C. for 30 min. The peptide-$^{188}$Re labeled pegylated liposomes were separated from free $^{188}$Re using PD-10 column (GE Healthcare) eluted with normal saline. Each 0.5 ml fraction was collected into a tube. The opacity of liposome was used to visually monitor the collection of the peptide-$^{188}$Re labeled pegylated liposomes. The labeling efficiency was determined by using the activity in peptide-pegylated-liposomes after separation divided by the total activity before separation. See also Chen et al., Anticancer Research 30:65-72 (2010).

EXAMPLE 3

Characterization of Designed Cancer-Target Peptides (i) Determining Peptide Binding Activity to GRP78 in an In Vitro Binding Assay 26 candidate peptides designed by the method described in Example 1 (listed in Table 6 below) above and peptide CdL, a negative control, were synthesized by conventional chemical synthesis and subjected to the surface-plasmon-resonance based method described below to examine the binding activities of the peptides to human GRP78.

The chip NTA and HBS-P buffer were obtained from GE Healthcare. Sensor chip NTA was prepared by combining Ni-ion chelation and covalent immobilization of N-His tagged GRP78 via amine-coupling with nitrilotriacetic acid on chip NTA (FIG. 6). To immobilize GRP78 protein on sensor chip for peptide-binding assay using Biacore, the methods based on Ni-ion chelation and amine coupling reaction were combined. Sensor chip NTA was prepared by chelation followed by covalent immobilization of N-His-tagged GRP78 via amine-coupling at the nitrilotriacetic acid group on chip NTA. The sensor chip NTA, HBS-P buffer and amine coupling kits were all obtained from GE Healthcare. First, the activation of chip surface using EDC and NHS reagents for amine coupling were according to the standard procedure from manufacturer's instruction. Additionally, one-minute pulse of $NiCl_2$ solution (500 μM) was used to attract His-tagged GRP78 to the surface of sensor chip and formed covalent bond subsequently in the condition of HBS-P buffer (pH 7.4). The resulting differences of RU were about 5,000-6,000 RU. After de-activation by ethanolamine and washed with EDTA (3 mM), the prepared sensor chip was then applied to Biacore X for binding assay. The HBS-P buffer containing 1 mM Gly was used as running buffer for binding assay. Solution of 20 mM sodium hydroxide dissolved in running buffer was used to regenerate the chip surface by one-minute pulse. Comparing with conventional methods using Ni-ion chelation alone, our chip surface exhibit more stable baseline and provide higher sensitivity for binding analysis of small molecules in Biacore X. This method was found to be better than that using chip CM5 because of its higher protein viability in oriented immobilization and without being exposed to low pH buffer during protein immobilization.

The sensor chip thus prepared was applied to Biacore X for determining the binding between the peptides and GRP78. The HBS-P buffer containing 1 mM Gly was used as a running buffer. A solution of 20 mM sodium hydroxide dissolved in the running buffer was used to regenerate chip surface by 1-minute pulses. The results obtained from this study were shown in Table 6 below.

TABLE 6

Biacore binding assay of 26 peptide analogs of L-peptide at 50 μM against full-length recombinant GRP78

| Alterations at Pro11 | ID | Sequence | HotLig score (rank) | Binding index |
|---|---|---|---|---|
| Positive control | L-peptide | RLLDTNRPLLPY (SEQ ID No: 13) | −27.65 (14) | 1.00 |
| Negative control | CdL | RLLDTNRPL(d-L)PY (SEQ ID No: 13) | — | <0.2 |
| *Hydrophobic* | | | | |
| Pro | P-6 | RLLDTNRPFLPY (SEQ ID No: 3) | −28.56 (6) | 1.1~1.52 |
| | PA-1 | RLLDTNRPWLPY (SEQ ID No: 14) | - | 0.35 |
| | PA-2 | RLLDTNRPELPY (SEQ ID No: 15) | - | <0.2 |
| | PA-3 | RLLDTNRPDLPY (SEQ ID No: 16) | - | <0.2 |
| | PA-4 | RLLDTNRPNLPY (SEQ ID No: 17) | - | 0.31 |
| | PA-5 | RLLDTNRPQLPY (SEQ ID No: 18) | - | 0.3 |
| | PA-6 | RLLDTNRPHLPY (SEQ ID No: 19) | - | 0.47 |
| | PB-3 | RLLDTNRPLLPY(CONH$_2$) (SEQ ID No: 13) | - | 1.15 |
| Trp | P-12 | RLLDTNRPHLWY (SEQ ID No: 4) | −27.79 (12) | 1.2~3.5 |
| | PB-1 | RLLDTNRPFLWY (SEQ ID No: 11) | - | 1.6 |
| | PB-2 | RLLDTNRPYLWY (SEQ ID No: 12) | - | 3 |
| Phe | P-4 | RLLDTNRPKLFY (SEQ ID No: 23) | −28.68 (4) | <0.2 |
| | P-7 | RLLDTNRPSLFY (SEQ ID No: 25) | −28.46 (7) | <0.2 |
| | P-13 | RLLDTNRPFLFY (SEQ ID No: 5) | −27.70 (13) | 1.4~3.5 |
| Leu | P-14 | RLLDTNRPLLLY (SEQ ID No: 30) | −26.72 (29) | 0.21 |
| Val | P-2 | RLLDTNRPKLVY (SEQ ID No: 21) | −31.18 (2) | <0.2 |
| | P-3 | RLLDTNRPQLVY (SEQ ID No: 22) | −29.66 (3) | <0.2 |
| *Positive charged* | | | | |
| Lys | P-1 | RLLDTNRPYLKY (SEQ ID No: 20) | −33.46 (1) | <0.2 |
| | P-8 | RLLDTNRPMLKY (SEQ ID No: 26) | −28.04 (8) | <0.2 |
| | P-10 | RLLDTNRPFLKY (SEQ ID No: 28) | −27.89 (10) | <0.2 |
| | P-15 | RLLDTNRPHLKY (SEQ ID No: 31) | −27.52 (16) | <0.2 |
| Arg | P-16 | RLLDTNRPKLRY (SEQ ID No: 32) | −27.42 (20) | <0.2 |
| *Negative charged* | | | | |
| Glu | P-17 | RLLDTNRPRLEY (SEQ ID No: 33) | −26.78 (27) | <0.2 |
| *Other* | | | | |
| Met | P-5 | RLLDTNRPMLMY (SEQ ID No: 24) | −28.58 (5) | <0.2 |
| Cys | P-9 | RLLDTNRPPLCY (SEQ ID No: 27) | −27.99 (9) | <0.2 |
| Gly | P-11 | RLLDTNRPLLGY (SEQ ID No: 29) | −27.87 (11) | 0.77 |

A representative sensorgram of peptide binding to the full-length recombinant GRP78 is shown in FIG. 4, panel a. It was shown that peptides P-12, P-6, and P-13 bound to GRP78 better than the L-peptide in the assay. The binding of various peptides to GRP78 is also shown as a binding index in Table 6. The binding index represents the difference of resonance units (RUs) divided by the molecular weight of each peptide and was normalized by comparison to the L-peptide. Six of these peptides were found to exhibit significant binding responses in Biacore including P-6, P-12, P-13, PB-1, PB-2, and PB-3 (Table 6). When compared to the L-peptide, the structure-activity relationships at the 9th amino acid of the L-peptide revealed that an increase in the hydrophobicity led to enhancement of the binding affinity (e.g., L-peptide and P-6). However, a Trp-substitution at the 9th site (e.g., PA-1) significantly decreased the binding, probably due to steric hindrance. For other hydrophilic peptides (e.g., PA-2 to PA-6), Glu-, Asp-, Asn-, Gln-, and His-substituted peptides also showed lower binding affinities than the L-peptide.

On the other hand, only Pro and aromatic residues such as Phe and Trp at the 11th amino acid were found to be able to bind to GRP78 (e.g., L-peptide, P-6, P-12, P-13, PB-1, and PB-2), because any other amino acid substitution at this position led to a decrease in the binding affinity. In particular, the charged amino acids substituted at either the 9th or 11th position of the L-peptide resulted in a loss of binding ability. Additionally, modification of the carboxylic acid terminus of the L-peptide, such as PB-3 in Table 6, did not significantly affect the binding affinity as Compared to the L-peptide.

Three optimized peptides, P-6, P-12, and P-13, were used for further in vitro and in vivo evaluations of their cancer-targeting abilities.

(ii) Binding of FITC-Labeled Peptides to Cancer Cells

To evaluate the in vitro binding abilities of cancer-targeting peptides described herein, the FITC-labeled L-peptide, P-6, P-12, P-13, and P-16 were tested for their binding activities to cancer cells, primary breast cancer engrafted in NOD/SCID mice, and clinical breast cancer specimens by a flow cytometric analysis as described below.

Cells were grown to 80% confluence and harvested with 5 mmol/L EDTA in PBS. Breast cancer specimens were obtained from patients who underwent initial surgery at Tri-Service General Hospital (Taipei, Taiwan). The clinical breast cancer specimens were sliced to fragments of 1 mm2 in size and subjected to enzymatic digestion by collagenase (1,000 U/mL), hyaluronidase (300 U/mL), and DNase I (100 µg/mL) at 37° C. for 2 hours. Primary breast tumor cells were collected after filtration through a 100 µm cell strainer (BD Biosciences) and re-suspended. For transplantation, tumor cells mixed with normal human breast fibroblasts and Matrigel were subcutaneously injected into mammary fat pads of female NOD/SCID mice received a sub-lethal dose of gamma irradiation in advance. After transplantation, cells of xenografted tumors were isolated and inoculated in NOD/SCID mice for serial passages. The cancer cell lines, xenograft cells, and primary breast tumor cells were re-suspended in a FACS buffer (PBS with 2% fetal bovine serum) and incubated at room temperature for 30 min with FITC-conjugated various peptides. To determine breast cancer stem cell (BCSCs) and non-breast cancer stem cell (non-BCSC) populations from xenografts, the cells were stained with a mixture of anti-H2$K_d$-biotin followed by streptavidin-PER-CP, anti-CD24-PE, anti-CD44-APC and FITC-conjugated various peptides. The primary breast tumor cells were stained with anti-CD45-PerCP-Cy5.5 antibodies, instead of H2$K_d$ staining. The stained cells were then subjected to FACS analysis.

As shown in FIG. 7, panel b, L-peptide, P-6, P-12, and P-13 all bound to both MDA-MB-231 cells (breast cancer cells) and TW01 cells (nasopharyngeal carcinoma). The binding capacities of the L-peptide and the P-6, P-12, P-13, and P-16 peptides to two xenograft samples from NOD-SCID mice transplanted with human primary breast cancer cell lines BC0145 and BC0244 were evaluated with special focus on their binding to the BCSC subpopulation enriched from the breast cancer cells. Breast cancer cells harvested from engrafted tumors were stained with H2$K_d$ to gate out mouse cells, and stained with anti-CD24 and anti-CD44 antibodies to distinguish BCSC-enriched cells (CD24$^-$CD44$^+$) from non-BCSC cells. These cells were co-stained with one of the above-noted peptides, which was FITC-labeled and subjected to flow cytometric analysis. As shown in FIG. 7, panel c, these peptides were able to bind both the BCSC-enriched population and the non-BSCS cells isolated from the two xenografts. P-13 stained most strongly, followed by P-6>P-12>L>P-16, although the binding capacity of P6 was equivalent to P-12 to BCSC-enriched cells isolated from the BC0145 xenograft. The binding abilities of these peptides to clinical breast specimens were similar to those to xenograft samples. The tested peptides were found to bind to both BCSC-enriched (CD45$^-$CD44$^+$CD24$^-$) and non-BCSC (the remaining CD45$^-$ cells) cells isolated from samples BC0854 and BC0861. FIG. 7, panel d. These results demonstrated that the peptides tested in this study are capable of binding to BCSCs isolated from xenografts of primary breast cancer and clinical breast cancer specimens, suggesting that they target the BCSC-enriched subpopulation. Moreover, P-13, P-12, and P-6 displayed greater binding capacities in vitro than L-peptide to both BCSCs and non-BCSCs, indicating that they are more effective than the L-peptide in targeting cancer cells.

(iii) Use of Cancer-Targeting Peptides for Tumor Imaging

Peptide-linked liposomes containing $^{188}$Re were used to evaluate the tumor-targeting abilities of the L-peptide and the peptides identified in Example 1 above by microSPECT/CT imaging of BC0244 xenografts. Briefly, NOD-SCID female mice were subcutaneously injected with 1×10$^6$ BC0244 cells in the right hind flank. After one month, BC0244 xenograft-bearing mice were intravenously injected with 400 µCi of $^{188}$Re-liposome-L-peptide, $^{188}$Re-liposome-P-6, $^{188}$Re-liposome-P-12, $^{188}$Re-liposome-P-13, or $^{188}$Re-liposome alone, all of which were prepared following the methods described in Example 2 above. Six, twenty-four, and forty-eight hours after the intravenously injection, microSPECT images were acquired using a microSPECT/CT scanner system as described in Rajarshi Guha et al. *J. Chem. Inf. Model.* 46:991-998; 2006. The standardized uptake value (SUV) was calculated to determine the uptake of radioactivity in tumors using the formula:

$$SUV = [\text{mean ROI activity}(\mu Ci/g)] / [\text{injected activity} (\mu Ci)/\text{mouse body weight}(g)].$$

Two-way ANOVA with Bonferroni's multiple comparison test was used to analyze microSPECT/CT imaging data. Mixed model was used to analyze the differences of growth rate tendency between various groups. Kaplan-Meier method and log-rank test were used to analyze the survival data. One-way ANOVA with Bonferroni's multiple comparison test was used to analyze the body weight data. Statistical significance was taken as $p<0.05$. All statistical analyses were done using the SPSS statistical software (SPSS Inc., Chicago, Ill.).

As shown in Table 7 below, there were significantly greater uptake of $^{188}$Re-liposome-P-6 ($p<0.05$) at 6 h, $^{188}$Re-liposome-L-peptide ($p<0.01$) at 24 h, as well as $^{188}$Re-liposome-P-6 ($p<0.001$), Re-liposome-P-12 ($p<0.01$), and $^{188}$Re-liposome-P-13 ($p<0.05$) at 48 h, as compared to the $^{188}$Re-liposomes in BC0244 tumors at all time points. At 48 h, the uptake of P-6-linked $^{188}$Re-liposomes was higher than that of the L-peptide, indicating its better tumor targeting abilities ($p<0.001$).

TABLE 7

Uptake of peptide-conjugated $^{188}$Re-liposomes in Xenograft NOD-SCID Mice

| Time points | $^{188}$Re-liposome-L | $^{188}$Re-liposome-P-6 | $^{188}$Re-liposome-P-12 | $^{188}$Re-liposome-P-13 | $^{188}$Re-liposome |
|---|---|---|---|---|---|
| 6 h | 1.58 ± 0.54 | 2.26 ± 0.14$^{a*,b***}$ | 1.59 ± 0.37 | 1.79 ± 0.21 | 1 |
| 24 h | 2.92 ± 0.42$^{a**}$ | 2.09 ± 0.10 | 1.71 ± 0.15 | 1.79 ± 0.45 | 1 |
| 48 h | 1.07 ± 0.30 | 3.68 ± 0.41$^{a***}$ | 2.21 ± 0.39$^{a**}$ | 2.26 ± 0.76$^{a*}$ | 1 |

(iv) Therapeutic Efficacy of Peptide-Labeled Liposomal Doxorubicin

The cancer-targeting activities of the peptides disclosed herein in targeted cancer chemotherapy was examined as follows, using the L-peptide as a positive control. The L-peptide was found to bind to a variety of tumor cell lines and cancer tissues from cancer patients. See Tables 8-10 below:

TABLE 8

Binding of FITC-L-peptide to a variety of tumor cell lines

| Binding ability | Cancer type | Cell line |
|---|---|---|
| positive | Nasopharyngeal | TW01, TW06, TW07 |
| | Breast | MDA-MB-231, T47D, MB157, AU565 |
| | Lung | H1299, A549 |
| | Prostate | LNCap.FGC, PC-3 |
| | Melanoma | M14 |
| | Immortalized fetal kidney epithelium containing T antigen | 293T |
| | Ovarian | 2008 |
| | Cervix epithelial | Hela |
| | Testicular embryonal | Ntera-2-cl.DI |
| negative | Leukemia | CEM, K562, Jurkat, HL-60 |
| | Osteosarcoma | Saos2 |
| | Colon | HT-29, LoVo, LS174T |
| | Hepatocyte | HepG2 |
| | Glioblastoma | G9T/VGH, U-373 |
| | Neuroblastoma | Be2c |

TABLE 9

Clinical histopathological characteristics of breast cancer patients and their corresponding L-peptide binding capacities to tumors.

| Coding NO. | Age | Stage | Tumor type(Histological grade) | Grade | ER* | PR* | HER2/neu* | L peptide (Differences in MFI)[#] |
|---|---|---|---|---|---|---|---|---|
| BC0634 | 53 | IIIA | invasive ductal carcinoma | 3 | − | + | + | 1.39 |
| BC0643 | 65 | IIB | Invasive ductal carcinoma | 3 | − | + | − | 2.12 |
| BC0679 | 46 | IIIB | Invasive ductal carcinoma | 2 | + | + | − | 2.58 |
| BC0697 | 50 | IIA | Invasive ductal carcinoma | 3 | − | + | − | 2.71 |
| BC0775 | 68 | IIA | Invasive ductal carcinoma | 3 | + | + | + | 0 |
| BC0854 | 53 | IIB | Invasive ductal carcinoma | 3 | + | + | − | 7.67 |
| BC0859 | 49 | IIIA | Invasive ductal carcinoma with apocrine differentiation and EIC (high grade, 30%). | 3 | − | − | w+ | 0.92 |
| BC0861 | 57 | IIB | Invasive ductal carcinoma | 3 | − | − | + | 5.11 |
| BC0866 | 36 | IIIC | Invasive ductal carcinoma with DCIS, high grade (15%). | 3 | + | + | + | 14.3 |
| VBC039 | 71 | II | Invasive ductal carcinoma | 3 | + | + | − | 2 |
| VBC040 | 68 | II | Invasive ductal carcinoma | 2 | + | + | − | 47.54 |

TABLE 10

Biodistribution of L-peptide-linked PEG-liposome containing [188]Re in NOD-SCID mice

| 188Re-liposome-L-peptide(% ID/g) | 1 hr | 4 hr | 8 hr | 24 hr | 48 hr | 72 hr |
|---|---|---|---|---|---|---|
| Whole Blood | 55.93 ± 1.51 | 35.46 ± 2.88 | 27.03 ± 0.47 | 6.36 ± 0.73 | 0.68 ± 0.06 | 0.09 ± 0.01 |
| Tumor | 2.12 ± 0.42 | 4.64 ± 0.67 | 7.28 ± 0.01 | 4.01 ± 1.11 | 2.31 ± 0.27 | 2.11 ± 0.05 |
| Pituitary | 2.91 ± 0.93 | 5.72 ± 1.99 | 4.02 ± 0.32 | 1.20 ± 0.32 | 1.01 ± 0.96 | 0.28 ± 0.06 |
| L intestine | 1.23 ± 0.10 | 1.48 ± 0.19 | 1.22 ± 0.09 | 1.38 ± 0.29 | 0.44 ± 0.40 | 0.27 ± 0.17 |
| S intestine | 9.63 ± 2.76 | 15.59 ± 1.53 | 17.43 ± 0.06 | 9.88 ± 2.20 | 4.97 ± 2.34 | 2.85 ± 0.87 |
| Muscle | 0.58 ± 0.08 | 1.52 ± 0.86 | 0.53 ± 7.93 | 0.46 ± 0.10 | 0.15 ± 0.05 | 0.11 ± 0.00 |
| Bone | 1.94 ± 0.42 | 2.81 ± 0.65 | 1.75 ± 1.28 | 1.10 ± 0.23 | 1.33 ± 0.87 | 2.07 ± 0.64 |
| Pancreas | 2.24 ± 0.18 | 1.90 ± 0.30 | 1.85 ± 0.21 | 1.16 ± 0.20 | 0.29 ± 0.16 | 0.07 ± 0.01 |
| Spleen | 10.76 ± 0.12 | 12.05 ± 3.31 | 14.62 ± 0.08 | 3.08 ± 3.10 | 7.77 ± 4.01 | 6.80 ± 2.06 |
| Adrenals | 5.98 ± 0.66 | 8.51 ± 1.92 | 4.73 ± 0.27 | 1.79 ± 0.36 | 3.01 ± 1.13 | 3.44 ± 2.55 |
| Kidney | 9.73 ± 0.51 | 9.06 ± 2.16 | 7.68 ± 0.11 | 4.27 ± 0.51 | 2.38 ± 1.02 | 1.77 ± 0.07 |
| Lung | 12.63 ± 1.03 | 8.97 ± 1.93 | 6.11 ± 0.62 | 2.08 ± 0.23 | 0.58 ± 0.27 | 0.73 ± 0.16 |
| Heart | 4.63 ± 0.18 | 4.53 ± 0.61 | 4.40 ± 0.04 | 2.59 ± 0.43 | 0.91 ± 0.49 | 1.29 ± 0.09 |
| Liver | 13.26 ± 0.07 | 20.19 ± 3.33 | 62.33 ± 0.73 | 3.55 ± 2.11 | 9.33 ± 3.90 | 6.85 ± 0.92 |
| Feces | 0.18 ± 0.03 | 8.48 ± 3.62 | 12.20 ± 0.33 | 0.62 ± 2.49 | 13.02 ± 5.25 | 7.00 ± 0.50 |
| S intestine content | 1.25 ± 0.30 | 1.67 ± 0.33 | 1.61 ± 4.55 | 1.68 ± 0.13 | 1.59 ± 0.74 | 0.20 ± 0.07 |
| Brain | 0.79 ± 0.05 | 0.74 ± 0.21 | 0.47 ± 1.20 | 0.12 ± 0.02 | 0.02 ± 0.01 | 0.01 ± 0.00 |
| Balder | 1.09 ± 0.16 | 1.27 ± 0.27 | 1.67 ± 3.90 | 0.81 ± 0.15 | 1.10 ± 0.53 | 0.55 ± 0.22 |
| Tu/Mu | 3.96 ± 0.95 | 14.56 ± 1.55 | 14.32 ± 6.01 | 6.73 ± 2.81 | 34.96 ± 20.96 | 24.93 ± 12.23 |

PEGylated P-6, P-12, and P-13 were coupled with liposomal doxorubicin (P-6-Lipo-Dox, P-12-Lipo-Dox, and P-13-Lipo-Dox) following the method described in Example 2 above. NOD-SCID female mice were subcutaneously injected with 1×10[6] BC0244 xenograft cells into mammary fat pad. Mice with size-matched tumors (approximate 100 mm$^3$) (n=5) were randomly assigned to different treatment groups and intravenously injected with PBS, liposomal doxorubicin (Lipo-Dox), L-peptide-linked Lipo-Dox (L-peptide-Lipo-Dox), P-6-Lipo-Dox, P-12-Lipo-Dox, or P-13-Lipo-Dox. The dosage of doxorubicin was 2 mg/kg injected once every week for three weeks. Mouse body weight and tumor size were measured twice a week with calipers. The tumor volumes were calculated using the equation: length×(width)$^2$×0.5.

Figure 8:
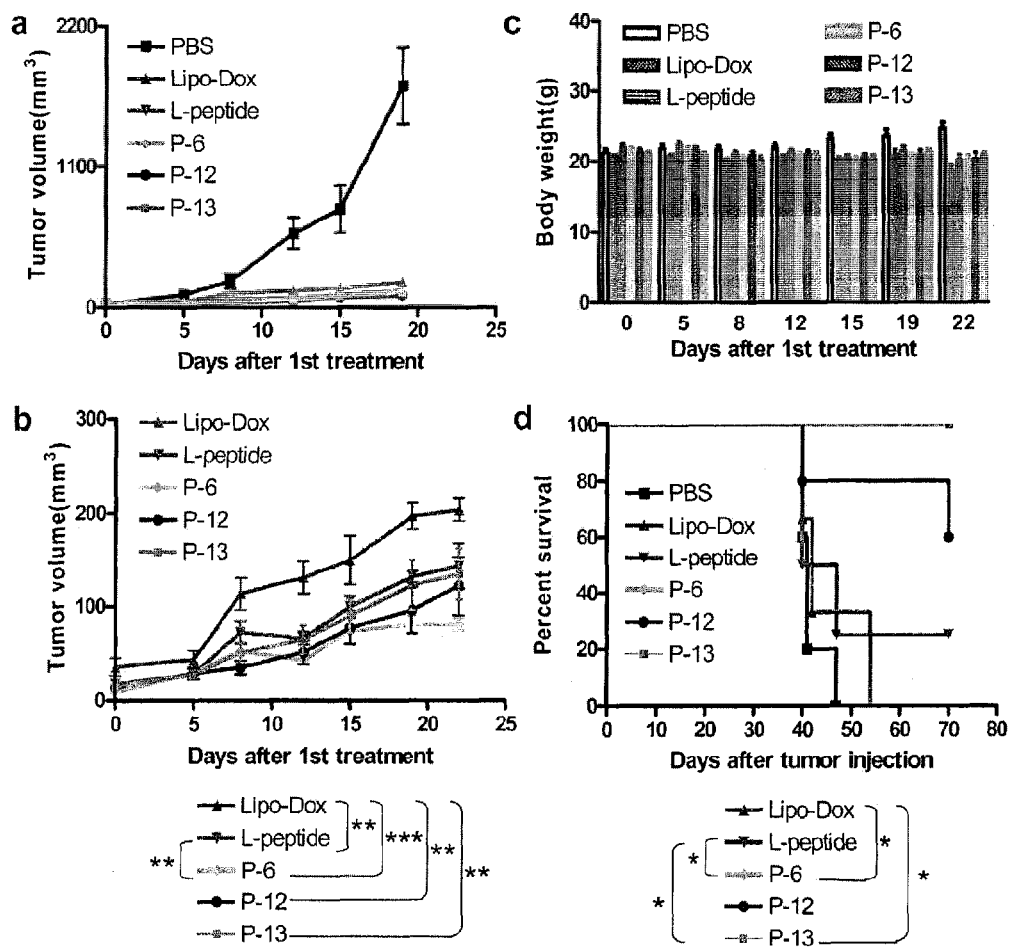
FIG. 8 is a diagram showing therapeutic efficacy of Lipo-Dox linked to L-peptide (n=4), P-6 (n=4), P-12 (n=7), or P-13 (n=6) in NOD/SCID mice bearing BC0244 human breast cancer xenografts. a and b: tumor size measured twice a week. c: body weight, measured twice a week. d: Kaplan Meier survival curve of mice treated with PBS, Lipo-Dox, or peptides-labeled Lipo-Dox. *, P<0.05; , P<0.01; *, P<0.001 of peptides-labeled Lipo-Dox compared with Lipo-Dox.

The results obtained from this study indicate that Lipo-Dox significantly suppressed tumor growth in xenografted mice as compared to PBS (p<0.0001) (FIG. 8, panel a) and the peptide-conjugated Lipo-Dox further suppressed tumor growth, indicating that targeted chemotherapy using any of the tested cancer-targeting peptides enhanced the efficacy of doxorubicin therapy. (FIG. 8, panel b). To be more specific, the tumor growth rates in mice treated with L-peptide-Lipo-Dox, P-6-Lipo-Dox, P-12-Lipo-Dox, and P-13-Lipo-Dox groups, and Lipo-Dox were reduced by 66.90%, 37.37%, 67.13%, and 65.00%, respectively, as compared to that in mice treated with PBS. FIG. 8, panel b. Moreover, treatment with P-6-lipo-Dox suppressed the tumor growth rate to 55.86% of that of the L-peptide-Lipo-Dox group (p=0.0012). FIG. 8, panel b. Survival rates of tumor-bearing mice after various treatments were monitored over 70 days. The results show that the survival of P-6-Lipo-Dox and P-13-Lipo-Dox groups were significantly longer than the L-peptide-Lipo-Dox group (p=0.0388 and p=0.0221, respectively). FIG. 8, panel d. The body weight of tumor-bearing mice receiving PBS gradually increased due to the growing weight of the tumors; however, the body weight of the other five groups did not change significantly. FIG. 8, panel c.

Taken together, the results discussed above demonstrate that the tested cancer-targeting peptides enhanced chemotherapy efficacy by targeting chemotherapy drugs to tumor sites and that the cancer-targeting activities of these peptides, such as P6 and P13, are unexpectedly higher than that of the L-peptide.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. An isolated peptide consisting essentially of the amino acid sequence RLLDTNRPX$_1$LX$_2$Y (SEQ ID NO:2), in which X$_1$ is H or an amino acid with a hydrophobic side chain, X$_2$ is P, F, or W, wherein when X$_1$ is L, X$_2$ is not P, and when X$_2$ is P, X$_1$ is not L, and wherein the peptide binds to human glucose-regulated protein 78 (GRP-78).

2. The isolated peptide of claim 1, wherein X$_1$ is L, H, F, or W.

3. The isolated peptide of claim 1, wherein the peptide is RLLDTNRPX$_1$LX$_2$Y (SEQ ID NO:2).

4. The isolated peptide of claim 1, wherein the peptide consisting essentially of an amino acid sequence selected from the group consisting of RLLDTNRPFLPY (P-6) (SEQ ID NO:3), RLLDTNRPHLWY (P-12) (SEQ ID NO:4), RLLDTNRPFLFY (P-13) (SEQ ID NO:5), RLLDTNRPFLWY (PB-1) (SEQ ID No:11) and RLLDTNRPYLWY (PB-2) (SEQ ID No:12).

5. The isolated peptide of claim 4, wherein the peptide is selected from the group consisting of RLLDTNRPFLPY (P-6) (SEQ ID NO:3), RLLDTNRPHLWY (P-12) (SEQ ID NO:4), RLLDTNRPFLFY (P-13) (SEQ ID NO:5), RLLDTNRPFLWY (PB-1) (SEQ ID No:11) and RLLDTNRPYLWY (PB-2) (SEQ ID No:12).

6. A composition comprising (a) the peptide of claim 1, and (b) an anti-cancer agent.

7. The composition of claim 6, wherein the composition further comprises a vehicle carrier.

8. The composition of claim 7, wherein the vehicle carrier is a liposome, which encapsulates the anti-cancer agent, and wherein the peptide is attached on the surface of the liposome.

9. The composition of claim 6, wherein the peptide is pegylated.

10. The composition of claim 6, wherein the composition comprises an anti-cancer agent, which is doxorubicin, vinorelbine, vincristine, paclitaxel or lurtotecan.

11. The composition of claim 6, wherein the composition is a pharmaceutical composition, which further comprises a pharmaceutically acceptable carrier.

12. A method for delivering an anti-cancer agent to cancer cells, comprising contacting cancer cells or cells that express GRP-78 with the composition of claim 6.

13. The method of claim 12, wherein the contacting step is performed by administering the composition to a subject having or suspected of having cancer cells expressing GRP-78.

14. The method of claim 13, wherein the cancer cells expressing GRP-78 are breast cancer cells, hepatocellular carcinoma cells, prostate cancer cells, lung cancer cells, ovarian cancer cells, kidney cancer cells, uterine cervical cancer cells, melanoma cells, embryonal carcinoma cells, leukemia cells, or osteosarcoma cells.

15. The method of claim 13, wherein the subject has or is suspected of having breast cancer stem cells expressing GRP-78.

16. The method of claim 12, wherein the composition comprises an anti-cancer agent in an amount effective in treating cancer.

17. A method for treating cancer that expresses GRP-78, comprising administering to a subject in need thereof the composition of claim 11, wherein the composition comprises anti-cancer agent attached to the peptide, and wherein the anti-cancer agent is in an amount effective in treating cancer.

18. The method of claim 17, wherein the composition further comprises a liposome, which encapsulates the anti-cancer agent, and wherein the peptide is attached on the surface of the liposome.

19. The isolated peptide of claim 1, wherein the peptide includes up to 50 amino acid residues.

20. The isolated peptide of claim 19, wherein the peptide includes up to 20 amino acid residues.

* * * * *

SEQUENCE LISTING

<160> NUMBER OF SEQ ID NOS: 33

<210> SEQ ID NO 1
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(2)

<223> OTHER INFORMATION: Residue may be H or an amino acid with a
      hydrophobic side chain
<220> FEATURE:
<221> NAME/KEY: MISC_FEATURE
<222> LOCATION: (4)..(4)
<223> OTHER INFORMATION: Residue may be P, F, or W

<400> SEQUENCE: 1

Pro Xaa Leu Xaa
1

<210> SEQ ID NO 2
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (9)..(9)
<223> OTHER INFORMATION: Variable position
<220> FEATURE:
<221> NAME/KEY: MISC_FEATURE
<222> LOCATION: (11)..(11)
<223> OTHER INFORMATION: Variable position

<400> SEQUENCE: 2

Arg Leu Leu Asp Thr Asn Arg Pro Xaa Leu Xaa Tyr
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 3

Arg Leu Leu Asp Thr Asn Arg Pro Phe Leu Pro Tyr
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 4

Arg Leu Leu Asp Thr Asn Arg Pro His Leu Trp Tyr
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 5

Arg Leu Leu Asp Thr Asn Arg Pro Phe Leu Phe Tyr
1               5                   10

<210> SEQ ID NO 6
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 6

Pro Phe Leu Pro
1

<210> SEQ ID NO 7
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 7

Pro His Leu Trp
1

<210> SEQ ID NO 8
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 8

Pro Phe Leu Trp
1

<210> SEQ ID NO 9
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 9

Pro Tyr Leu Trp
1

<210> SEQ ID NO 10
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 10

Pro Phe Leu Phe
1

<210> SEQ ID NO 11
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 11

Arg Leu Leu Asp Thr Asn Arg Pro Phe Leu Trp Tyr
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Synthetic Polypeptide

```
<400> SEQUENCE: 12

Arg Leu Leu Asp Thr Asn Arg Pro Phe Leu Phe Tyr
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 13

Arg Leu Leu Asp Thr Asn Arg Pro Leu Leu Pro Tyr
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 14

Arg Leu Leu Asp Thr Asn Arg Pro Trp Leu Pro Tyr
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 15

Arg Leu Leu Asp Thr Asn Arg Pro Glu Leu Pro Tyr
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 16

Arg Leu Leu Asp Thr Asn Arg Pro Asp Leu Pro Tyr
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 17

Arg Leu Leu Asp Thr Asn Arg Pro Asn Leu Pro Tyr
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 18
```

```
Arg Leu Leu Asp Thr Asn Arg Pro Gln Leu Pro Tyr
1               5                   10
```

<210> SEQ ID NO 19
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 19

```
Arg Leu Leu Asp Thr Asn Arg Pro His Leu Pro Tyr
1               5                   10
```

<210> SEQ ID NO 20
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 20

```
Arg Leu Leu Asp Thr Asn Arg Pro Tyr Leu Lys Tyr
1               5                   10
```

<210> SEQ ID NO 21
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 21

```
Arg Leu Leu Asp Thr Asn Arg Pro Lys Leu Val Tyr
1               5                   10
```

<210> SEQ ID NO 22
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 22

```
Arg Leu Leu Asp Thr Asn Arg Pro Gln Leu Val Tyr
1               5                   10
```

<210> SEQ ID NO 23
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 23

```
Arg Leu Leu Asp Thr Asn Arg Pro Lys Leu Phe Tyr
1               5                   10
```

<210> SEQ ID NO 24
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 24

Arg Leu Leu Asp Thr Asn Arg Pro Met Leu Met Tyr
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 25

Arg Leu Leu Asp Thr Asn Arg Pro Ser Leu Phe Tyr
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 26

Arg Leu Leu Asp Thr Asn Arg Pro Met Leu Lys Tyr
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 27

Arg Leu Leu Asp Thr Asn Arg Pro Pro Leu Cys Tyr
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 28

Arg Leu Leu Asp Thr Asn Arg Pro Phe Leu Lys Tyr
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 29

Arg Leu Leu Asp Thr Asn Arg Pro Leu Leu Gly Tyr
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 30

Arg Leu Leu Asp Thr Asn Arg Pro Leu Leu Leu Tyr

```
<210> SEQ ID NO 31
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 31

Arg Leu Leu Asp Thr Asn Arg Pro His Leu Lys Tyr
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 32

Arg Leu Leu Asp Thr Asn Arg Pro Lys Leu Arg Tyr
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 33

Arg Leu Leu Asp Thr Asn Arg Pro Arg Leu Glu Tyr
1               5                   10
```